(12) United States Patent
Brown

(10) Patent No.: US 6,968,375 B1
(45) Date of Patent: *Nov. 22, 2005

(54) NETWORKED SYSTEM FOR INTERACTIVE COMMUNICATION AND REMOTE MONITORING OF INDIVIDUALS

(75) Inventor: Stephen J. Brown, Woodside, CA (US)

(73) Assignee: Health Hero Network, Inc., Mountain View, CA (US)

(*) Notice: Subject to any disclaimer, the term of this patent is extended or adjusted under 35 U.S.C. 154(b) by 860 days.

This patent is subject to a terminal disclaimer.

(21) Appl. No.: 09/658,209

(22) Filed: Sep. 8, 2000

Related U.S. Application Data

(63) Continuation-in-part of application No. 09/300,856, filed on Apr. 28, 1999, now Pat. No. 6,368,273, which is a division of application No. 08/946,341, filed on Oct. 7, 1997, now Pat. No. 5,997,476, which is a continuation-in-part of application No. 08/847,009, filed on Apr. 30, 1997, now Pat. No. 5,897,493.

(60) Provisional application No. 60/041,746, filed on Mar. 28, 1997, and provisional application No. 60/041,751, filed on Mar. 28, 1997.

(51) Int. Cl.$^7$ ............................................. G06F 15/173
(52) U.S. Cl. ...................... 709/224; 709/217; 709/203; 705/3; 600/301
(58) Field of Search ................................ 709/224, 203, 709/217; 705/3, 2; 600/301, 300; 379/106.2

(56) References Cited

U.S. PATENT DOCUMENTS

| | | |
|---|---|---|
| 3,426,150 A | 2/1969 | Tygart |
| 3,566,365 A | 2/1971 | Rawson et al. |
| 3,566,370 A | 2/1971 | Worthington, Jr. et al. |
| 3,768,014 A | 10/1973 | Smith et al. ............ 324/158 R |
| 3,910,257 A | 10/1975 | Fletcher et al. |
| 3,920,005 A | 11/1975 | Gombrich et al. |
| 3,996,928 A | 12/1976 | Marx |
| 4,004,577 A | 1/1977 | Sarnoff |
| 4,130,881 A | 12/1978 | Haessler et al. |
| 4,150,284 A | 4/1979 | Trenkler et al. |
| 4,151,407 A | 4/1979 | McBride et al. |
| 4,151,831 A | 5/1979 | Lester |

(Continued)

FOREIGN PATENT DOCUMENTS

| | | |
|---|---|---|
| EP | 0251520 | 7/1988 |
| EP | 0286456 | 10/1988 |

(Continued)

OTHER PUBLICATIONS

"+5V Powered Isolated RS–232 Drivers/Receivers" Maxim Integrated Products.

(Continued)

*Primary Examiner*—Ario Etienne
*Assistant Examiner*—Abdullahi E. Salad
(74) *Attorney, Agent, or Firm*—Morgan, Lewis & Bockius LLP; Craig P. Opperman

(57) ABSTRACT

A system for remotely monitoring an individual. The system includes a server system for generating a script program from a set of queries. The script program is executable by a remote apparatus that displays information and/or a set of queries to the individual through a user interface. Responses to the queries that are entered through the user interface together with individual identification information are sent from the remote apparatus to the server system across a communication network. The server system also includes an automated answering service for providing a series of questions from a stored set of questions for an individual at the remote apparatus to respond to, storing responses to each provided question in the series of questions and providing a service based on the individual's response to the questions.

67 Claims, 19 Drawing Sheets

U.S. PATENT DOCUMENTS

| | | |
|---|---|---|
| 4,173,971 A | 11/1979 | Karz |
| 4,216,462 A | 8/1980 | McGrath et al. |
| 4,227,526 A | 10/1980 | Goss |
| 4,253,521 A | 3/1981 | Savage |
| 4,259,548 A | 3/1981 | Fahey et al. |
| 4,270,547 A | 6/1981 | Steffen et al. |
| 4,296,756 A | 10/1981 | Dunning et al. |
| 4,347,568 A | 8/1982 | Giguere et al. |
| 4,347,851 A | 9/1982 | Jundanian |
| 4,360,345 A | 11/1982 | Hon |
| 4,417,306 A | 11/1983 | Citron et al. |
| 4,422,081 A | 12/1983 | Woods et al. |
| 4,449,536 A | 5/1984 | Weaver |
| 4,465,077 A | 8/1984 | Schneider |
| 4,473,884 A | 9/1984 | Behl |
| 4,519,398 A | 5/1985 | Lisiecki et al. |
| 4,531,527 A | 7/1985 | Reinhold, Jr. et al. |
| 4,546,436 A | 10/1985 | Schneider et al. |
| 4,566,461 A | 1/1986 | Lubell et al. |
| 4,576,578 A | 3/1986 | Parker et al. |
| 4,592,546 A | 6/1986 | Fascenda et al. |
| 4,627,445 A | 12/1986 | Garcia et al. ............... 128/770 |
| 4,674,652 A | 6/1987 | Aten et al. |
| 4,686,624 A | 8/1987 | Blum et al. .................. 364/415 |
| 4,694,490 A | 9/1987 | Harvey et al. |
| 4,695,954 A | 9/1987 | Rose et al. |
| 4,712,562 A | 12/1987 | Ohayon et al. |
| 4,722,349 A | 2/1988 | Baumberg |
| 4,729,381 A | 3/1988 | Harada et al. |
| 4,731,726 A | 3/1988 | Allen, III ................... 364/416 |
| 4,768,229 A | 8/1988 | Benjamin et al. |
| 4,779,199 A | 10/1988 | Yoneda et al. |
| 4,782,511 A | 11/1988 | Nemec et al. |
| 4,796,639 A | 1/1989 | Snow et al. |
| 4,799,199 A | 1/1989 | Scales, III et al. |
| 4,803,625 A * | 2/1989 | Fu et al. ..................... 600/483 |
| 4,835,372 A | 5/1989 | Gombrich et al. .......... 235/375 |
| 4,838,275 A * | 6/1989 | Lee ............................ 600/483 |
| 4,858,354 A | 8/1989 | Gettler |
| 4,858,617 A | 8/1989 | Sanders ...................... 128/696 |
| 4,890,621 A | 1/1990 | Hakky ........................ 125/635 |
| 4,897,869 A | 1/1990 | Takahashi |
| 4,907,973 A | 3/1990 | Hon |
| 4,933,873 A | 6/1990 | Kaufman et al. |
| 4,950,246 A | 8/1990 | Muller |
| 4,953,552 A | 9/1990 | DeMarzo .................... 128/635 |
| 4,958,632 A | 9/1990 | Duggan ................ 128/419 PG |
| 4,958,641 A | 9/1990 | Digby et al. |
| 4,967,756 A | 11/1990 | Hewitt |
| 4,977,899 A | 12/1990 | Digby et al. |
| 4,979,509 A | 12/1990 | Hakky ........................ 128/635 |
| 5,007,429 A | 4/1991 | Treatch et al. |
| 5,016,172 A | 5/1991 | Dessertine |
| 5,019,974 A | 5/1991 | Beckers |
| 5,024,225 A | 6/1991 | Fang |
| 5,025,374 A | 6/1991 | Roizen et al. |
| 5,034,807 A | 7/1991 | Von Kohorn |
| 5,036,462 A | 7/1991 | Kaufman et al. ...... 364/413.01 |
| 5,049,487 A | 9/1991 | Phillips et al. ................. 435/4 |
| 5,050,612 A | 9/1991 | Matsumura ................. 128/670 |
| 5,056,059 A | 10/1991 | Tivig et al. |
| 5,059,394 A | 10/1991 | Phillips et al. ............. 422/68.1 |
| 5,065,315 A | 11/1991 | Garcia |
| 5,068,536 A | 11/1991 | Rosenthal |
| 5,074,317 A | 12/1991 | Bondell et al. |
| 5,077,476 A | 12/1991 | Rosenthal |
| 5,095,798 A | 3/1992 | Okada et al. |
| 5,109,414 A | 4/1992 | Harvey et al. |
| 5,109,974 A | 5/1992 | Beer et al. |
| 5,111,396 A | 5/1992 | Mills et al. |
| 5,111,817 A | 5/1992 | Clark et al. |
| 5,111,818 A | 5/1992 | Suzuki et al. ............... 128/644 |
| 5,120,230 A | 6/1992 | Clark et al. |
| 5,120,421 A | 6/1992 | Glass et al. ................. 204/406 |
| 5,128,752 A | 7/1992 | Von Kohorn |
| 5,134,391 A | 7/1992 | Okada |
| 5,142,358 A | 8/1992 | Jason |
| 5,142,484 A | 8/1992 | Kaufman et al. |
| 5,176,502 A | 1/1993 | Sanderson et al. |
| 5,182,707 A | 1/1993 | Cooper et al. |
| 5,204,670 A | 4/1993 | Stinton |
| 5,222,020 A | 6/1993 | Takeda |
| 5,227,874 A | 7/1993 | Von Kohorn |
| 5,228,450 A | 7/1993 | Sellers |
| 5,231,990 A | 8/1993 | Gauglitz |
| 5,249,044 A | 9/1993 | Von Kohorn |
| 5,251,126 A | 10/1993 | Kahn et al. ............. 364/413.11 |
| 5,261,401 A | 11/1993 | Baker et al. .................... 607/9 |
| 5,262,943 A | 11/1993 | Thibado et al. |
| 5,265,888 A | 11/1993 | Yamamoto et al. ......... 273/434 |
| 5,266,179 A | 11/1993 | Nankai et al. .............. 204/401 |
| 5,275,159 A | 1/1994 | Griebel ....................... 128/633 |
| 5,282,950 A | 2/1994 | Dietze et al. ............... 204/406 |
| 5,299,121 A | 3/1994 | Brill et al. |
| 5,301,105 A * | 4/1994 | Cummings, Jr. ................ 705/2 |
| 5,304,468 A | 4/1994 | Phillips et al. ................ 435/14 |
| 5,307,263 A | 4/1994 | Brown ................... 364/413.09 |
| 5,309,919 A | 5/1994 | Snell et al. .................. 128/697 |
| 5,329,459 A | 7/1994 | Kaufman et al. |
| 5,329,608 A | 7/1994 | Bocchiere et al. |
| 5,331,549 A * | 7/1994 | Crawford, Jr. .............. 600/513 |
| 5,339,821 A | 8/1994 | Fujimoto |
| 5,341,291 A | 8/1994 | Roizen et al. |
| 5,343,239 A | 8/1994 | Lappington et al. |
| 5,344,324 A | 9/1994 | O'Donnell et al. |
| 5,357,427 A | 10/1994 | Langen et al. |
| 5,366,896 A | 11/1994 | Margrey et al. |
| 5,371,687 A | 12/1994 | Holmes, II et al. ......... 364/514 |
| 5,375,604 A | 12/1994 | Kelly et al. |
| 5,377,100 A | 12/1994 | Pope et al. |
| 5,390,238 A * | 2/1995 | Kirk et al. .............. 379/106.02 |
| 5,399,821 A | 3/1995 | Inagaki et al. |
| 5,410,471 A * | 4/1995 | Alyfuku et al. ............. 600/300 |
| 5,410,474 A | 4/1995 | Fox ....................... 364/413.07 |
| 5,429,140 A | 7/1995 | Burdea et al. |
| 5,431,691 A | 7/1995 | Snell et al. .................... 607/27 |
| 5,434,611 A | 7/1995 | Tamura |
| 5,438,607 A | 8/1995 | Przygoda, Jr. et al. |
| 5,441,047 A | 8/1995 | David et al. |
| 5,454,721 A | 10/1995 | Kuch |
| 5,454,722 A | 10/1995 | Holland et al. |
| 5,456,606 A | 10/1995 | McIntyre |
| 5,456,692 A | 10/1995 | Smith, Jr. et al. ............. 607/31 |
| 5,458,123 A | 10/1995 | Unger |
| 5,467,269 A | 11/1995 | Flaten |
| 5,471,039 A | 11/1995 | Irwin, Jr. et al. |
| 5,483,276 A | 1/1996 | Brooks et al. |
| 5,488,412 A | 1/1996 | Majeti et al. |
| 5,488,423 A | 1/1996 | Walkingshaw et al. |
| 5,501,231 A | 3/1996 | Kaish |
| 5,502,636 A | 3/1996 | Clarke |
| 5,502,726 A | 3/1996 | Fischer |
| 5,504,519 A | 4/1996 | Remillard |
| 5,517,405 A | 5/1996 | McAndrew et al. |
| 5,518,001 A | 5/1996 | Snell |
| 5,519,433 A | 5/1996 | Lappington et al. |
| 5,544,649 A | 8/1996 | David et al. |
| 5,546,943 A | 8/1996 | Gould |
| 5,549,117 A | 8/1996 | Tacklind et al. |
| 5,550,575 A | 8/1996 | West et al. |
| 5,553,609 A | 9/1996 | Chen |

| | | |
|---|---|---|
| 5,558,638 A | 9/1996 | Evers et al. |
| 5,564,429 A | 10/1996 | Bornn et al. |
| 5,569,212 A | 10/1996 | Brown |
| 5,572,421 A | 11/1996 | Altman et al. |
| 5,574,828 A | 11/1996 | Hayward et al. |
| 5,576,952 A | 11/1996 | Stutman et al. |
| 5,590,648 A | 1/1997 | Mitchell et al. |
| 5,596,994 A * | 1/1997 | Bro .......................... 600/545 |
| 5,597,307 A | 1/1997 | Redford et al. |
| 5,601,435 A | 2/1997 | Quy |
| 5,613,495 A | 3/1997 | Mills et al. |
| 5,619,991 A | 4/1997 | Sloane |
| 5,624,265 A | 4/1997 | Redford et al. |
| 5,628,309 A | 5/1997 | Brown |
| 5,629,981 A | 5/1997 | Nerlikar ...................... 380/25 |
| 5,631,844 A | 5/1997 | Magrey et al. |
| 5,633,910 A | 5/1997 | Cohen |
| 5,640,953 A | 6/1997 | Bishop et al. |
| 5,642,731 A | 7/1997 | Kehr |
| 5,642,936 A | 7/1997 | Evans |
| 5,666,487 A | 9/1997 | Goodman et al. |
| 5,670,711 A | 9/1997 | Detournay et al. |
| 5,675,635 A | 10/1997 | Vos et al. |
| 5,678,562 A | 10/1997 | Sellers |
| 5,678,571 A | 10/1997 | Brown |
| 5,687,322 A | 11/1997 | Deaton et al. |
| 5,687,717 A | 11/1997 | Halpern et al. |
| 5,687,734 A | 11/1997 | Dempsey et al. |
| 5,704,364 A | 1/1998 | Saltzstein et al. |
| 5,704,366 A | 1/1998 | Tacklind et al. |
| 5,704,902 A | 1/1998 | Vandenbelt et al. |
| 5,711,297 A | 1/1998 | Iliff |
| 5,715,451 A | 2/1998 | Marlin |
| 5,715,823 A | 2/1998 | Wood et al. |
| 5,717,913 A | 2/1998 | Driscoll |
| 5,720,733 A | 2/1998 | Brown |
| 5,722,418 A | 3/1998 | Bro |
| 5,727,153 A | 3/1998 | Powell |
| 5,730,124 A | 3/1998 | Yamauchi .................. 128/630 |
| 5,732,696 A | 3/1998 | Rapoport et al. |
| 5,732,709 A | 3/1998 | Tacklind et al. |
| 5,734,413 A | 3/1998 | Lappington et al. |
| 5,752,234 A | 5/1998 | Withers |
| 5,760,771 A | 6/1998 | Blonder et al. |
| 5,772,585 A | 6/1998 | Lavin et al. |
| 5,778,882 A | 7/1998 | Raymond et al. |
| 5,782,814 A | 7/1998 | Brown et al. |
| 5,785,650 A | 7/1998 | Akasaka et al. |
| 5,791,342 A | 8/1998 | Woodard |
| 5,792,117 A | 8/1998 | Brown |
| 5,793,969 A | 8/1998 | Kamentsky et al. |
| 5,796,393 A | 8/1998 | MacNaughton |
| 5,802,494 A | 9/1998 | Kuno |
| 5,810,747 A | 9/1998 | Brudny et al. |
| 5,819,735 A | 10/1998 | Mansfield et al. |
| 5,822,544 A | 10/1998 | Chaco et al. |
| 5,825,283 A | 10/1998 | Camhi |
| 5,827,180 A | 10/1998 | Goodman |
| 5,828,943 A | 10/1998 | Brown |
| 5,835,896 A | 11/1998 | Fisher et al. |
| 5,868,669 A | 2/1999 | Iliff |
| 5,875,432 A | 2/1999 | Sehr |
| 5,879,163 A | 3/1999 | Brown et al. |
| 5,893,077 A | 4/1999 | Griffin |
| 5,893,098 A | 4/1999 | Peters et al. |
| 5,897,493 A | 4/1999 | Brown |
| 5,899,855 A | 5/1999 | Brown |
| 5,911,687 A | 6/1999 | Sato et al. |
| 5,913,310 A | 6/1999 | Brown |
| 5,918,603 A | 7/1999 | Brown |
| 5,920,477 A | 7/1999 | Hoffberg et al. |
| 5,933,136 A | 8/1999 | Brown |
| 5,941,829 A | 8/1999 | Saltzstein et al. |
| 5,961,446 A | 10/1999 | Beller et al. |
| 5,983,217 A | 11/1999 | Khosravi-Sichani et al. |
| 5,987,471 A | 11/1999 | Bodine et al. |
| 5,995,969 A | 11/1999 | Lee et al. |
| 5,997,476 A | 12/1999 | Brown |
| 6,001,065 A | 12/1999 | DeVito |
| 6,022,315 A | 2/2000 | Iliff |
| 6,022,615 A | 2/2000 | Rettenbacher |
| 6,029,138 A | 2/2000 | Khorasani et al. |
| 6,035,328 A * | 3/2000 | Soukal ....................... 709/217 |
| 6,046,761 A | 4/2000 | Echerer |
| 6,049,794 A | 4/2000 | Jacobs et al. |
| 6,050,940 A | 4/2000 | Braun et al. |
| 6,055,314 A | 4/2000 | Spies et al. |
| 6,055,487 A | 4/2000 | Margery et al. |
| 6,055,506 A | 4/2000 | Frasca, Jr. |
| 6,057,758 A | 5/2000 | Dempsey et al. |
| 6,110,148 A | 8/2000 | Brown et al. |
| 6,138,145 A | 10/2000 | Kawanaka |
| 6,151,586 A | 11/2000 | Brown |
| 6,168,563 B1 | 1/2001 | Brown |
| 6,177,940 B1 | 1/2001 | Bond et al. |
| 6,189,029 B1 | 2/2001 | Fuerst |
| 6,221,012 B1 | 4/2001 | Maschke et al. ............ 600/301 |
| 6,248,065 B1 | 6/2001 | Brown |
| 6,368,273 B1 * | 4/2002 | Brown ....................... 600/300 |

FOREIGN PATENT DOCUMENTS

| | | | |
|---|---|---|---|
| EP | 0320749 | 2/1989 | |
| EP | 370599 | 5/1990 | |
| EP | 0461910 | 12/1991 | |
| EP | 508912 | 10/1992 | |
| EP | 526166 | 2/1993 | |
| EP | 0 653 718 A2 | 11/1994 | ........... G06F/19/00 |
| EP | 676709 | 10/1995 | |
| EP | 680727 | 11/1995 | |
| EP | 761160 | 3/1997 | |
| GB | 2218831 | 11/1989 | |
| GB | 2 225 637 A | 6/1990 | ............ A61B/5/02 |
| WO | WO-8501667 | 4/1985 | |
| WO | WO 90/00367 | 1/1990 | ............ A61B/5/05 |
| WO | WO-9109374 | 6/1991 | |
| WO | WO 93/01489 | 1/1993 | .......... G01N/25/48 |
| WO | WO-9302622 | 2/1993 | |
| WO | WO-9416774 | 8/1994 | |
| WO | WO-95/09386 | 4/1995 | |
| WO | WO-95/20199 | 7/1995 | |
| WO | WO-9529447 | 11/1995 | |
| WO | WO 96/07908 A1 | 3/1996 | .......... G01N/33/52 |
| WO | WO-96/25877 | 8/1996 | |
| WO | WO-97/08605 | 3/1997 | |
| WO | WO-97/12544 | 4/1997 | |
| WO | WO-98/16895 | 4/1998 | |

OTHER PUBLICATIONS

"CD–ROM Mavericks: Proprietary TV–Based Players", *Byte Guide to CD–ROM*, pp. 100–105.

"European Search Report", From 6858P005EP, (Mar. 27, 1998).

"Introducing the Next Generation of About Your Diabetes", *U.S. Pharmacopcial Convention and American Diabetes Association*, (1993).

"The description of the Tandy Radio Shack TRS–80 Model 100/102 device available at http://www.old–computers.com/museum/computer.asp?c=233", *World Wide Wed*, (Feb. 13, 2004),1–3.

Anonymous, "Health Hero netowrk, inc. Receivers First–Ever FDA Clearance for Connecting Medical Devices to Internet", *PR Newswire*, (Dec. 2, 1999),3 pages.

Bower, "Brain Clues to Energy–efficient Learning", *Science News*, (Apr. 1992), v 141; p215(1); Dialog: File 647, Acct# 12123949.

Bruce, "Health Hero Network CEO, CNNfn", *Digital Jam*, (Dec. 1, 1999),3 pages

Bruce, et al., "The Effects of Sympathetic Nervous System Activation and Psychological Stress . . . ", *Diabetologia*, (1992),.; ; 35(9); 835–843; Dialog: File 5, Acc# 9629427.

Cheng, Joe H., "PCT Search Report", (Jan. 11, 1996).

Finston, "Parent+Teacher=Healty Child", *Diabetes Forecast*, (Apr. 1994), v47 n9; P26(5); Dialog: file 149, Acc# 15804228.

Fox, "Not My Type: Type B Behavior, Type 1 Diabetes Plus Stress Equals Blood Sugar Blues", *Health*, (Mar. 1988),v20 n3; pp22(1); Dialog: File 149, Acc# 06397959.

Frieberger, Paul, "Video Game Takes on Diabetes Superhero "Captain Novolin" Offers Treatment Tips", *San Francisco Examiner*, (Jun. 26, 1992),Fourth Edition, Business Section B1.

Giuffrida, Antonio, et al., "Should We Pay the Patient? Review of Financial Incentives to enhance Patient compliance", *Biomedical Journal*, (1997),vol. 315, pp. 703–707.

Hauben, Jay R., "A Brief History of the Cleveland Free–Net", available at http://www.ais.org/~irh/acn7–1.a09.html, (1995),pp. 1–4.

Hunter, "Technological Advances in Bedside Monitoring: Biosensors", *Archives and Laboratory Medicine*, (Jul. 1987),pp. 633–636.

Kauffmann, Francine, et al., "Epidermiological Study of the Genetics and Environment of Asthma, Bronchial Hyperresponsiveness and Atopy", *Am. J. Respir. Crit. Care Med.*, (1997), vol. 156, pp. S123–S129.

Kaufman, Steven, "B., The Learning Game", *Nation's Business*, (Nov. 1993).

Lacyk, John, "PCT Search Report", (Jun. 12, 1997).

Marsh, David G., "Approaches Toward the Genetic Analysis of Complex Traits Asthma and Atop", *Am. J. Respir.Crit. Care Med.*, (1997),vol. 156, pp. S–133–S138.

Martinez, Fernando D., "Complexities of the Genetics of Asthma", *Am. J. Respir. Crit. Care Med.*, (1997),vol. 156, pp. S117–S122.

Mazzola, et al., "Video Diabetes: A Teaching Tool for Children with Insulin–Dependent Diabetes", *Proceedings— 7th Annual Symposium on Computer Applications in Medical Care; Washington, DC; Dialog:*, (Oct. 1983),File 8, Acc# 01624462.

Meissner, et al., "Building an Integrated Clinical and Research Network", *Proceedings of the SPIE*, (Oct. 24, 1995),vol. 2618, p. 92 99.

Moore, "New Applications Break Through Storage Boundaries", *Computer Technology Review*, (Oct. 1999),vol. 19, No. 10. p. 1.

Reis, Howard, "Telemedicine: Transmitting Expertise to the Point of Care", *Proceedings: Toward an Electronic Patient Record*, (1997), pp. 248–256.

Roberts;, "Diabetes and Stress: A Type A Connection?", *Psychology Today*, (Jul. 1987), v. 21; pp22(1); Dialog: File 149, Acc# 05038381.

Schenkels, P., "Supplementary European Search Report", Application No. EP 97 92 2716, (Mar. 11, 2002).

Schork, Nicholas J., "Genetics of Complex Disease", *Am. J. Respir. Crit. Care Med.*, (1997),vol. 156, pp. s103–S109.

Shandle, Jack, "Who Will dominate the desktop In the 90s?", *Electronics*, (Feb. 1990),pp. 48–50.

Voelker, Rebecca, "Shoe Leather Therapy is Gaining on TB", *Jama*, (Mar. 13, 1996), vol. 275, 743.

A. Caprihan, et al., "A Simple Microccomputer for Biomedical Signal Processing," *IECI '78 Annual Conference Proceedings on Industrial Applications of Microprocessors*, Mar. 20–22, 1978, pp. 18–23.

J. Stuart Soeldner, "Treatment of Diabetes Mellitus by Devices," *The American Journal of Medicine*, Jan. 1981, vol. 70, pp. 183–194.

Kuykendall, V. G., et al., "Assessment of Self–Monitored Blood Glucose Results Using a Reflectance Meter with memory and Microcomputer," *Symposium on Computer Applications in Medical Care*, 9th:1985:Baltimore, M.D., pp. 98–102.

Blood Glucose Monitors, Portable, Health Device, V. 17(9), 253–271 (1988).

Daisuke Yoshizawa, et al., "The Development of a Data processing System with Personal Computer of MSX Standard System for Flow Injection Analysis," *Journal of Flow Injection Analysis*, 1988, V. 5, No. 2, pp. 101–110.

A.S. Douglas, et al., ":Hand–held Glucose Monitor and Recorder," *Proceedings of the Annual International Conference of the IEEE Engineering in Medicine and Biology Society*, Nov. 4–7, 1988, New Orleans, LA, pp. 747–748.

Stuart J. Updike, et al, "Laboratory Evaluation of New Reusable Blood Glucose Sensor," *Diabetes Care*, Nov./Dec. 1988, vol. 11, No. 10, pp. 801–807.

"Central Fetal Monitoring Systems with Optical Disk Storage," *New Technology Brief*, Nov./Dec. 1988, vol. 2, No. 6, pp. 249–251.

Beverly J. Leyerle, et al., "The PDMS as a Focal Point for Distributed Patient Data," *International Journal of Clinical Monitoring and Computing*, 1988, vol. 5, pp. 155–161.

A.M. Albisser, "Intelligent Instrumentation in Diabetic Management," *CRC Critical Reviews in Biomedical Engineering*, vol. 17, No. 1, pp. 1–24.

J. Schrezenmeir, et al., "Computer Assisted Insulin Dosage Adjustment—Perspectives for Diabetes Control," *Hormone and Metabolic Research*, 1990, Supplement Series vol. 24, pp. 116–123.

E.F. Pfeiffer, "The Glucose Sensor: The Missing Link in Diabetes Therapy," *Hormone and Metabolic Research*, 1990, vol. 24, Suppl., pp. 154–164.

Laughton E. Miles, "A Portable Microcomputer for Long–Term Physiological Monitoring in the Home and Work Environment," *Medical Monitoring in the Home and Work Environment*, 1990, pp. 47–57.

D.A. Valera, et al., "Accuracy of Portable Blood Glucose Monitoring," *American Journal of Clinical Patholoy*, 1991, vol. 95, No. 2, pp. 247–252.

P.G. Fabietti, et al., "Wearable System for Acquisition, Processing and Storage of the Signal from Amperometric Glucose Sensors," *The International Journal of Artificial Organs*, 1991, vol. 14, No. 3, pp. 175–178.

A. Billiard, et al., "Telematic Transmission of Computerized Blood Glucose Profiles for IDDM Patients," *Diabetes Care*, Feb. 1991, vol. 14, No. 2, pp. 130–134.

Latman, N. S., "Evaluation of Electronic, Digital Blood Glucose Monitors," *Biomedical Instrumentation and Technology*, 1991, vol. 25, No. 1, 43–49.

Thomas Hauser, et al., "Will Computers Replace or Complement the Diabetes Educator?," *The Medical Journal of Australia*, Oct. 5, 1992, vol. 157, 489–491.

V. L. Rose, et al., "Decentralized Testing for Prothrombin Time and Activated Partial Thromboplastin Time Using a Dry Chemistry Portable Analyser," *Archives of Pathology and Laboratory Medicine*, Jun. 1993, vol. 117, pp. 611–617.

V. Poitout, et al., "A Glucose Monitoring System for on line Estimation in Man of Blood Glucose Concentration Using a Miniaturized Glucose Sensor Implanted in the Subcutaneous Tissue and a Wearable Control Unit," *Diabetologia*, 1993, vol. 36, pp. 658–663.

P. Brunetti, et al., "A Simulation Study on a Self–tuning Portable Controller of Blood Glucose," *The International Journal of Artificial Organs*, 1993, vol. 16, No. 16, pp. 51–57.

Marc C. Shults, et al., "A Telemetry–Instrumentation System for Monitoring Multiple Subcutaneously Implanted Glucose Sensors," *IEEE Transactions on Biomedical Engineering*, Oct. 1994, vol. 41, No. 10, pp. 937–942.

Hiroyuki Horio, et al., "Clinical Telecommunication Network System for Home Monitoring", *Medical & Biological Engineering & Computing.*, Mar. 1994, vol. 32, 227–230.

David Potter, "Fundamentals of PC–Based Data Acquisition," *SENSORS*, Feb. 1994, pp 12–20.

M. Makikawa, et al., "Microprocessor–Based Memory Device for Ambulatory Heart Rate and Physical Activity Recording," *Methods of Information in Medicine*, 1994, vol. 33, No. 1, pp. 94–96.

J.C. Wyatt, "Clinical Data Systems, Part 2: Components and Techniques," *Lancet*, Dec. 1994, vol. 344, No. 8937, pp. 1609–1604.

"How Flash Memory Works," Internet Printout of URL address: http://www.howstuffworks.com/flash–memory4.htm, printed Sep. 28, 2002, 2 pages.

* cited by examiner

SCRIPT ENTRY SCREEN

SCRIPT NAME: DIABETES SCRIPT 1

| QUERIES | CHOICE 1 | CHOICE 2 | CHOICE 3 | CHOICE 4 |
|---|---|---|---|---|
| HOW DO YOU FEEL? | VERY BAD | BAD | GOOD | VERY GOOD |
| HOW WELL ARE YOU MANAGING YOUR DISEASE? | VERY BADLY | BADLY | WELL | VERY WELL |
| HOW HARD IS IT FOR YOU TO FOLLOW YOUR TREATMENT PLAN? | VERY HARD | HARD | EASY | VERY EASY |
| HOW HARD IS IT FOR YOU TO CONTROL YOUR BLOOD SUGAR? | VERY HARD | HARD | EASY | VERY EASY |

SELECT DEVICE TYPE(S)

[X] GLUCOSE METER  [ ] RESPIRATORY FLOW METER  [ ] BP CUFF

CONNECTION TIME: 03:00 ▽  [CREATE SCRIPT]  [CANCEL]

*FIG. 5*

NUMBER: 9001 {LF}     ⎧⁻⁴⁰

LED: 1 {LF}

ZAP: {LF}

CLS: {LF}

93 ⎧ DISPLAY: ANSWER QUERIES NOW?
　　　　　　PRESS ANY BUTTON TO START {LF}
　　⎨ WAIT: {LF}
　　⎩ CLS: {LF}

DISPLAY: HOW DO YOU FEEL?

VERY　　　　　　　VERY
      BAD　BAD　GOOD　GOOD {LF}

95 ⎧ INPUT: OOOO {LF}
　　⎪ CLS: {LF}
　　⎪ DISPLAY: HOW WELL ARE YOU
　　⎨ 　　　　　MANAGING YOUR DISEASE?
　　⎪ 　　　　　VERY　　　　　　　VERY
　　⎪ 　　　　　WELL　BADLY　WELL　WELL {LF}
　　⎩ INPUT: OOOO {LF}

CLS: {LF}

DISPLAY: HOW HARD IS IT FOR YOU TO
         FOLLOW YOUR TREATMENT PLAN?
         VERY　　　　　　　VERY
         HARD　HARD　EASY　EASY {LF}

INPUT: OOOO {LF}

CLS: {LF}

DISPLAY: HOW HARD IS IT FOR YOU TO
         CONTROL YOUR BLOOD SUGAR?
         VERY　　　　　　　VERY
         HARD　HARD　EASY　EASY {LF}

*FIG. 6A*

INPUT: 0000 {LF}

CLS: {LF}

DISPLAY: CONNECT GLUCOSE METER
AND PRESS ANY BUTTON
WHEN FINISHED {LF}

WAIT: {LF}

CLS: {LF}

DISPLAY: COLLECTING MEASUREMENTS {LF}

97 ~ COLLECT: GLUCOSE_METER {LF}

CLS: {LF}

DISPLAY: CONNECT APPARATUS TO
TELEPHONE JACK AND
PRESS ANY BUTTON
WHEN FINISHED {LF}

WAIT: {LF}

LED: 0 {LF}

CLS: {LF}

DELAY: 03:00 {LF}

DISPLAY: CONNECTING TO SERVER {LF}

CONNECT: {LF}

{EOF}

*FIG. 6B*

PATIENT REPORT

PATIENT: LINDSEY, DAN ▽    DATE OF MEASUREMENT: MARCH 15, 1997 ▽

QUERY RESPONSES

HOW DO YOU FEEL?
BAD

HOW WELL ARE YOU MANAGING YOUR DISEASE?
BADLY

HOW HARD IS IT FOR YOU TO FOLLOW YOUR TREATMENT PLAN?
HARD

HOW HARD IS IT FOR YOU TO CONTROL YOUR BLOOD SUGAR?
VERY HARD

*FIG. 10*

SCRIPT ENTRY SCREEN

SCRIPT NAME: DIABETES SCRIPT 2

| STATEMENTS | CHOICE 1 | CHOICE 2 | CHOICE 3 | CHOICE 4 |
|---|---|---|---|---|
| YOUR NEXT APPOINTMENT WITH <<INSERT PHYSICIAN_NAME>> IS ON <<INSERT APPOINTMENT_DATE>> | OK | | | |
| <<INSERT PATIENT_NAME>>, YOUR LAB RESULTS FOR HEMOGLOBIN ARE <<INSERT HbA1c_RESULT>> | OK | | | |
| <<INSERT PATIENT_NAME>>, REMEMBER TO EXERCISE CONSISTENTLY | OK | | | |

CONNECTION TIME: 03:00 ▽   CREATE SCRIPT   CANCEL

FIG. 19

NETWORKED SYSTEM FOR INTERACTIVE COMMUNICATION AND REMOTE MONITORING OF INDIVIDUALS

PRIORITY CLAIM

This application is a continuation-in-part of U.S. application Ser. No. 09/300,856, filed Apr. 28, 1999, now U.S. Pat. No. 6,368,273, issued Apr. 9, 2002, which application is a divisional of U.S. application Ser. No. 08/946,341, filed Oct. 7, 1997, now U.S. Pat. No. 5,997,476, issued Dec. 7, 1999, which application is a continuation-in-part of U.S. application Ser. No. 08/847,009, filed Apr. 30, 1997, now U.S. Pat. No. 5,897,493, issued Apr. 27, 1999, which application claims priority from U.S. Provisional Application No. 60/041,746, filed Mar. 28, 1997 and from U.S. Provisional Application No. 60/041,751, filed Mar. 28, 1997.

RELATED APPLICATIONS

This application is also related to U.S. application Ser. No. 09/531,237 filed on Mar. 22, 2000, now abandoned, which is a continuation-in-part of U.S. Pat. No. 6,368,273 filed on Apr. 28, 1999 and issued on Apr. 9, 2002 which is a divisional of U.S. Pat. No. 5,997,476 filed on Oct. 7, 1997 and issued on Dec. 07, 1999, which is a continuation-in-part of U.S. Pat. No. 5,897,493 filed on Apr. 30, 1997 and issued on Apr. 27, 1999. This application is also related to U.S. Pat. No. 6,270,455 filed on Nov. 30, 1998 and issued on Aug. 7, 2001, which is a continuation-in-part of U.S. Pat. No. 5,997,476 filed on Oct. 7, 1997 and issued on Dec. 07, 1999.

This application is also related to U.S. application Ser. No. 09/665,442 filed on Sep. 19, 2000 which is a continuation-in-part of U.S. Pat. No. 6,381,577 filed on Mar. 2, 2000 and issued on Apr. 30, 2002 which is related to U.S. Pat. No. 6,101,478 filed on Nov. 21, 1997 and issued on Aug. 8, 2000 which is a continuation-in-part of U.S. Pat. No. 5,897,493 filed on Apr. 30, 1997 and issued Apr. 27, 1999.

This application is also related to U.S. application Ser. No. 09/378,188 filed on Aug. 20, 1999, now abandoned, which relates to U.S. Pat. No. 6,101,478 filed on Nov. 21, 1997 and issued Aug. 8, 2000. U.S. application Ser. No. 09/378,188 is also related to U.S. Pat. No. 5,985,559 filed on May 3, 1997 and issued Nov. 16, 1999, which is a continuation-in-part of U.S. Pat. No. 5,897,493 filed on Apr. 30, 1997 and issued on Apr. 27, 1999.

This application also relates to U.S. Pat. No. 6,248,065 filed on Jan. 19, 1999 and issued on Jun. 19, 2001, which is a divisional application of U.S. Pat. No. 5,897,493 filed on Apr. 30,1997 and issued on Apr. 27, 1999.

This application is also related to U.S. application Ser. No. 10/279,749 filed on Oct. 23, 2002 which is related to U.S. application Ser. No. 10/233,296 filed on Aug. 30, 2002 which is related to U.S. application Ser. No. 09/713,922 filed on Aug. 15, 2000 which is a continuation-in-part of U.S. Pat. No. 6,381,577 filed on Mar. 2, 2000 and issued on Apr. 30, 2002.

This application is also related to U.S. application Ser. No. 10/233,296 filed on Aug. 30, 2002.

This application is also related to U.S. application Ser. No. 09/422,046 filed on Oct. 20, 1999 which claims priority from U.S. Pat. No. 6,168,563 filed on Mar. 27, 1999 and issued on Jan. 2, 2001, which is a continuation-in-part of U.S. Pat. No. 5,899,855 filed on Jun. 7, 1995 and issued on May 5, 1999.

FIELD OF THE INVENTION

The present invention relates generally to communication systems for remote monitoring of individuals, and in particular to a networked system for remotely monitoring individuals and for communicating information to the individuals through the use of script programs.

BACKGROUND OF THE INVENTION

In the United States alone; over 100 million people have chronic health conditions, accounting for an estimated $700 billion in annual medical costs. In an effort to control these medical costs, many healthcare providers have initiated outpatient or home healthcare programs for their patients. The potential benefits of these programs are particularly great for chronically ill patients who must treat their diseases on a daily basis. However, the success of these programs is dependent upon the ability of the healthcare providers to monitor the patients remotely to avert medical problems before they become complicated and costly. Further, success requires compliance with the program, which is often dependent on providing messages or other reminders to patients so that they will stay with the program. Unfortunately, no convenient and cost effective monitoring system exists to accomplish these objectives. While these problems are particularly acute for the poor and the elderly, all demographic groups could significantly benefit from remote communication and monitoring systems.

Prior attempts to monitor patients remotely have included the use of personal computers and modems to establish communication between patients and healthcare providers, either directly or via an Internet site. However, computers are too expensive to give away and the patients who already own computers are only a fraction of the total population.

Other attempts to monitor patients remotely have included the use of medical monitoring devices with built-in modems. Examples of such monitoring devices include blood glucose meters, respiratory flow meters, and heart rate monitors. While these devices can be quite successful, their multimedia capabilities arc often limited. In addition, many patients simply may prefer to interact with a device they are more familiar with, such as a television.

Prior attempts to monitor patients remotely have also included the use of interactive telephone or video response systems. Such interactive systems are disclosed in U.S. Pat. No. 5,39.0,238 issued to Kirk et al. on Feb. 14, 1995, U.S. Pat. No. 5,434,611 issued to Tamura on Jul. 18, 1995, and U.S. Pat. No. 5,441,047 issued to David et al. on Aug. 15, 1995. One disadvantage of these systems is that they either require a patient to call in to a central facility to be monitored or require the central facility to call the patient according to a rigid monitoring schedule.

If the patients are required to call the central facility, only the compliant patients will actually call regularly to be monitored. Non-compliant patients will typically wait until an emergency situation develops before contacting their healthcare provider, thus defeating the purpose of the monitoring system. If the central facility calls each patient according to a monitoring schedule, it is intrusive to the patient's life and resistance to the monitoring grows over time. Further, it is difficult to identify each patient uniquely using these systems. Moreover, these systems are generally incapable of collecting medical data from monitoring devices, such as blood glucose meters, respiratory flow meters, or heart rate monitors.

As such, there exists a need for a simple and inexpensive system for remotely monitoring patients and for easily communicating information to the patients. There is also a need to encourage patient's compliance with a prescribed treatment plan.

SUMMARY

The present invention provides a system for remotely interacting with an individual. The system includes a server, a remote interface device for assigning in the server a set of queries to be answered by the individual, a remotely programmable apparatus for interacting with the individual and a broadcaster in communication with the server and the remotely programmable apparatus.

By using the entertainment medium of interactive television with its ability to receive a large bandwidth of data, the present invention can more easily communicate interactive entertaining/educational information to potential and existing patients. The interactive nature of the received data makes it easy for a user to access interactive programs related to corresponding entertainment/advertisement content or related to user adherence to a predefined regimen.

In accordance with another aspect of the present invention, an answering service sends a series of questions as voice communication from a stored set of questions to the remote apparatus for the individual to respond to, when the voice communication button is activated. The answering service stores responses to each provided question in the series of questions and provides a service based on the individual's response to the questions. The provided service is communication with a health care professional or a service provider. Also, the answering service includes a speech recognition component for receiving spoken responses to the series of questions and a speech synthesis component for making the set of queries into a series of questions.

In accordance with yet another aspect of the present invention, the remotely programmable apparatus includes an appliance component for providing appliance functionality. The appliance component is an alarm clock, a kitchen appliance, or an entertainment device.

In accordance with still another aspect of the present invention, the remotely programmable apparatus includes a monitoring component for producing measurements of a physiological condition of the individual.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 5 is a script entry screen according to the preferred embodiment of the invention;

FIG. 6A is a listing of a sample script program according to the preferred embodiment of the invention;

FIG. 6B is a continuation of the listing of FIG. 6A;

FIG. 10 is a sample report displayed on a workstation of the system of FIGS. 1A–D;

FIG. 19 is a script entry screen according to an embodiment of the present invention;

DETAILED DESCRIPTION

Figure 1:
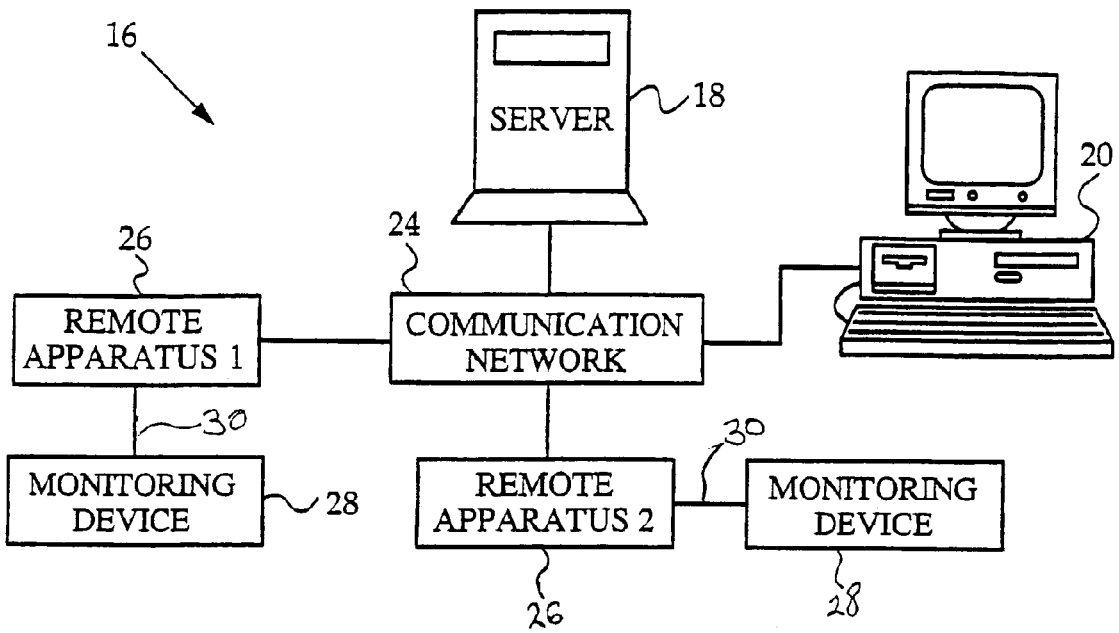
FIG. 1 is a block diagram of networked system formed in accordance with a first embodiment of the present invention.

The present invention provides a system and method for remotely monitoring individuals and for increasing individual use of health programs. In a first embodiment of the invention, the individuals are patients and the system is used to collect data relating to the health status of the patients. However, it is to be understood that the invention is not limited to remote monitoring of patients. The system and method of the invention may be used for any type of remote monitoring and program adherence application. The invention may also be implemented as an automated messaging system for communicating information to individuals, as will be discussed in an alternative embodiment below.

A first embodiment of the invention is illustrated in FIGS. 1A and 2–12. Referring to FIG. 1, a networked system 16 includes a server 18 and a workstation 20 connected to the 30 server 18 through a communication network 24. The server 18 is preferably a world wide web server and the communication network 24 is preferably the Internet. It will be apparent to one skilled in the art that the server 18 may comprise a single stand-alone computer or multiple computers distributed throughout a network. The workstation 20 is preferably a personal computer, remote terminal, or web TV unit connected to the server 18 via the Internet. The workstation 20 functions as a remote interface for entering in the server 18 messages and queries to be communicated to the patients.

The system 16 also includes multiple remotely programmable apparatus, such as first and second apparatuses 26 for monitoring multiple patients. Each apparatus 26 is designed to interact with a patient in accordance with script programs received from the server 18. Each apparatus 26 is in communication with the server 18 through the communication network 24, preferably the Internet. Alternatively, each apparatus 26 may be placed in communication with the server 18 via wireless communication networks, cellular networks, telephone networks, satellite networks or any other network which allows each apparatus 26 to exchange data with the server 18. It is to be understood that the system 16 may include any number of remotely programmable apparatuses for monitoring any number of patients.

In the preferred embodiment, each patient to be monitored is also provided with a monitoring device 28. The monitoring device 28 is designed to produce measurements of a physiological condition of the patient, record the measurements, and transmit the measurements to the patient's remotely programmable apparatus through a standard connection cable 30. Examples of suitable monitoring devices 28 include blood glucose meters, respiratory flow meters, blood pressure cuffs, electronic weight scales, and pulse rate monitors. Such monitoring devices are well known in the art. The specific type of monitoring device 28 provided to each patient is dependent upon the patient's disease or health treatment needs. For example, diabetes patients are provided with a blood glucose meter for measuring blood glucose concentrations, asthma patients are provided with respiratory flow meters for measuring peak flow rates, obesity patients are provided with weight scales, etc.

Figure 2:
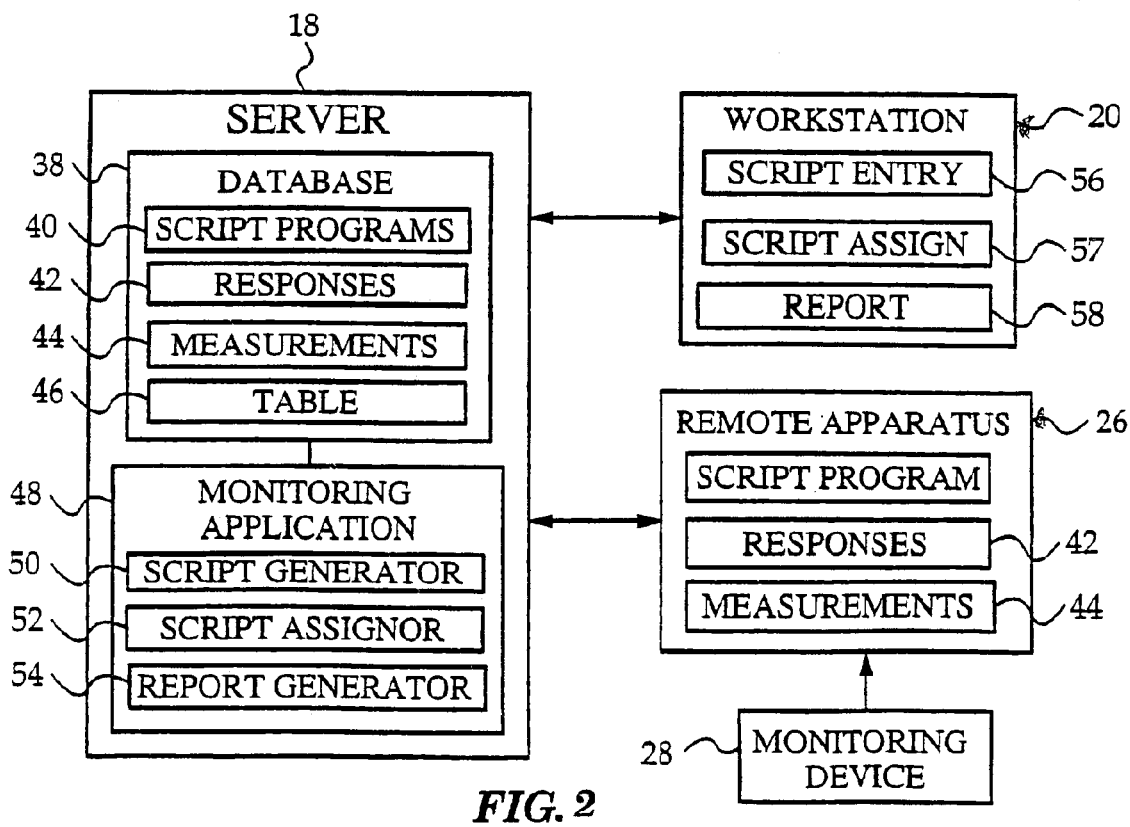
FIG. 2 is a block diagram illustrating the interaction of the components of the system of FIG. 1.

FIG. 2 shows the server 18, the workstation 20, and the apparatus 26 in greater detail. The server 18 includes a database 38 for storing programs 40. The script programs 40 are executed by each apparatus 26, to communicate queries and messages to a patient, receive responses 42 to the queries, collect monitoring device measurements 44, and to transmit responses 42 and measurements 44 to the server 18. The database 38 is designed to store responses 42 and measurements 44. The database 38 further includes a lookup table 46. The table 46 contains a list of the patients to be monitored, and for each patient, a unique patient identification code and a respective pointer to one or more script programs 40 assigned to the patient. Each remotely programmable apparatus 26 is designed to execute assigned script programs 40 received from the server 18. The script programs 40 may include queries, reminder messages, informational statements, useful quotations, or other information of benefit to the patient. See Appendix A for example script programs.

Figure 3:
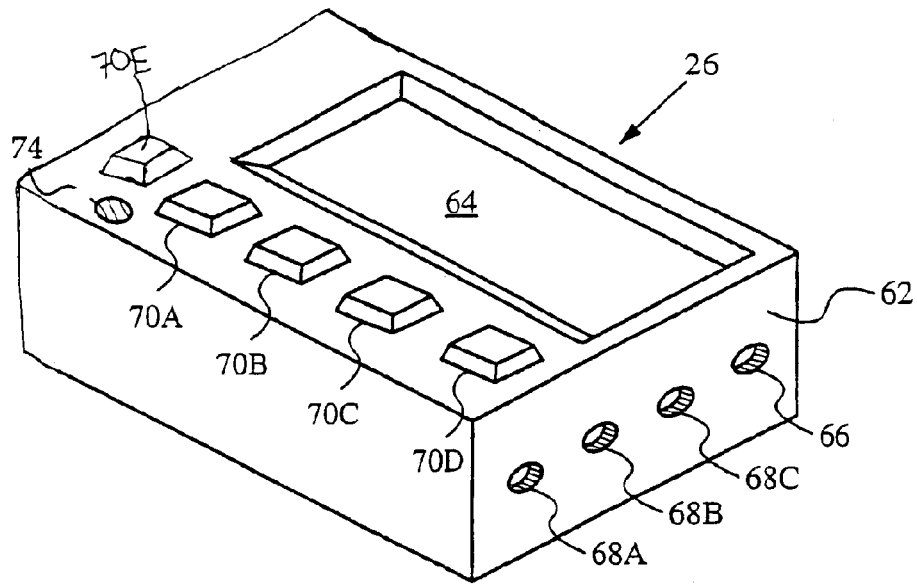
FIG. 3 is a perspective view of a remotely programmable apparatus of the system of FIG. 1.
Figure 4:
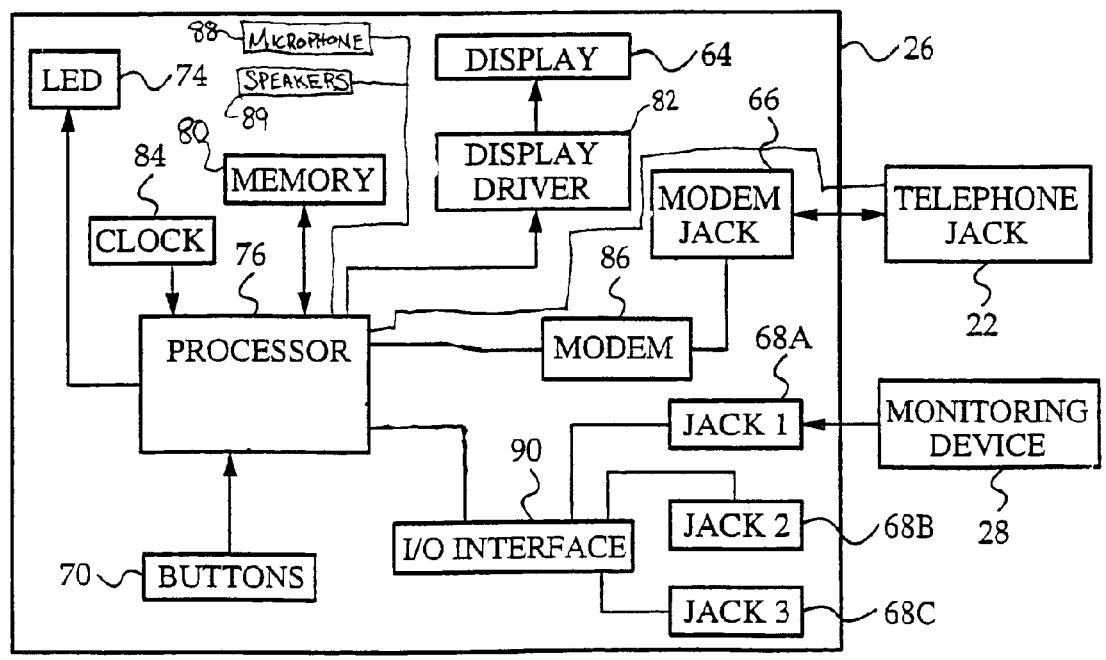
FIG. 4 is a block diagram illustrating the components of the apparatus of FIG. 3.

FIGS. 3–4 show the structure of a remotely programmable apparatus 26 according to the preferred embodiment. Referring to FIG. 3, the apparatus 26 includes a housing 62. The housing 62 is sufficiently compact to enable the apparatus 26 to be hand-held and carried by a patient. The apparatus 26 also includes a display 64 for displaying queries and prompts to the patient. In the preferred embodiment, the display 64 is a liquid crystal display (LCD).

The apparatus 26 includes five user input buttons 70A, 70B, 70C, 70D and 70E that are located on the same side of the apparatus 26 as the display 64. The user input buttons 70A–D are for entering in the apparatus 26 responses 42 to the queries and prompts. In the preferred embodiment, the user input buttons 70A–D are momentary contact push buttons. In alternative embodiments, user input buttons 70A–D may be replaced by switches, keys, a touch sensitive display screen, or any other data input device.

The user input button 70E is a emergency or other services button and is preferably red, but may be of any size, shape, or color that draws special visual or tactile attention to the user. The services provided by the user input button 70E are described in more detail below.

Three monitoring device jacks 68A, 68B, and 68C are located on a surface of housing 62. The device jacks 68A–C are for connecting the apparatus 26 to a number of monitoring devices 28, such as blood glucose meters, respiratory flow meters, or blood pressure cuffs (not shown in FIG. 3). The apparatus 26 also includes a modem jack 66 for connecting the apparatus 26 to a telephone jack through a standard connection cord (not shown). The apparatus 26 further includes a visual indicator, such as a light emitting diode (LED) 74. The LED 74 is for visually notifying the patient that he or she has unanswered queries stored in the apparatus 26.

FIG. 4 is a schematic block diagram illustrating the components of the apparatus 26 in greater detail. The apparatus 26 includes a microprocessor 76 and a memory 80 connected to the microprocessor 76. The memory 80 is preferably a non-volatile memory, such as a serial EEPROM. The memory 80 stores script programs 40 received from the server 18, measurements 44 received from the monitoring device 28, responses 42 to queries. The microprocessor 76 also includes built-in read only memory (ROM), which stores firmware for controlling the operation of the apparatus 26. The firmware includes a script interpreter used by the microprocessor 76 to execute the script programs 40. The script interpreter interprets script commands, which are executed by the microprocessor 76. Specific techniques for interpreting and executing script commands in this manner are well known in the art.

The microprocessor 76 is preferably connected to memory 80 using a standard two-wire interface. The microprocessor 76 is also connected to the user input buttons 70, the LED 74, a clock 84, and a display driver 82. The clock 84 indicates the current date and time to the microprocessor 76. For clarity of illustration, clock 84 is shown as a separate component, but is preferably built into the microprocessor 76. The display driver 82 operates under the control of the microprocessor 76 to display information on the display 64. The microprocessor 76 is preferably a PIC 16C65 processor. The modem 86 is connected to a telephone jack 22 through the modem jack 66. The modem 86 is for exchanging data between the server 18 and the processor 76 through the communication network 24. The data includes the script programs 40 which are received from the server 18 as well as the responses 42 to queries, the device measurements 44, the script identification codes, and the patient's unique identification code, which the modem 86 transmits to the server 18. The modem 86 is preferably a complete 28.8 K modem commercially available from Cermetek, although any suitable modem may be used. The processor 76 also includes a component that connects to the telephone jack 22 and a microphone 88 and a speaker 89, thereby allowing telephone calls to be processed.

The device interface 90 is connected to the device jacks 68A, 68B, and 68C. The device interface 90 is for interfacing with a number of monitoring devices 28, such as blood glucose meters, respiratory flow meters, blood pressure cuffs, weight scales, or pulse rate monitors; through device jacks 68A–C.

The device interface 90 operates under the control of the microprocessor 76 to collect measurements 44 from the monitoring devices 28 and to output the measurements to the microprocessor 76 for storage in the memory 80. In the preferred embodiment, the interface 90 is a standard RS232 interface. For simplicity of illustration, only one device interface 90 is shown in FIG. 4. However, in alternative embodiments, the apparatus 26 may include multiple device interfaces to accommodate monitoring devices that have different connection standards.

Referring again to FIG. 2, the server 18 includes a monitoring application 48. The monitoring application 48 is a controlling software application executed by the server 18 to perform the various functions described below. The application 48 includes a script generator 50, a script assignor 52, and a report generator 54. The script generator 50 is designed to generate the script programs 40 from script information entered through the workstation 20. The script information is entered through a script entry screen 56. In the preferred embodiment, script entry screen 56 is implemented as a web page on the server 18. The workstation 20 includes a web browser for accessing the web page to enter the script information.

FIG. 5 illustrates the script entry screen 56 as it appears on the workstation 20. The screen 56 includes a script name field 92 for specifying the name of a script program to be generated. The screen 56 also includes entry fields 94 for entering a set of queries to be answered by a patient. Each entry field 94 has corresponding response choice fields 96 for entering response choices for the query. The screen 56 further includes check boxes 98 for selecting a desired monitoring device 28, such as a blood glucose meter, respiratory flow meter, or blood pressure cuff, from which to collect measurements 44.

The screen 56 additionally includes a connection time field 100 for specifying a prescribed connection time at which each apparatus 26 executing the script is to establish a subsequent communication link to the server 18. The connection time is preferably selected to be the time at which communication rates are the lowest, such as 3:00 AM. The screen 56 also includes a CREATE SCRIPT button 102 for instructing script generator 50 to generate a script program 40 from the information entered in screen 56. The screen 56 further includes a CANCEL button 104 for canceling the information entered in screen 56.

In the preferred embodiment, each script program 40 created by script generator 50 conforms to the standard file format used on UNIX systems. In the standard file format, each command is listed in the upper case and followed by a colon. Every line in the script program 40 is terminated by a linefeed character {LF}, and only one command is placed on each line. The last character in the script program 40 is a UNIX end of file character {EOF}. Table 1 shows an exemplary listing of script commands used in the preferred embodiment of the invention.

TABLE 1

| SCRIPT COMMANDS | Command Description |
|---|---|
| CLS: {LF} | Clear the display. |
| ZAP: {LF} | Erase from memory the last set of query responses recorded. |
| LED: b{LF} | Turn the LED on or off, where b is a binary digit of 0 or 1. An argument of 1 turns on t0he LED, and an argument of 0 turns off the LED. |
| DISPLAY: {chars} {LF} | Display the text following the DISPLAY command. |
| INPUT: mmmm{LF} | Record a button press. The m's represent a button mask pattern for each of the four input buttons. Each m contains an "X" for disallowed buttons or an "O" for allowed buttons. For example, INPUT: OXOX{LF} allows the user to press either button #1 or #3. |

TABLE 1-continued

| SCRIPT COMMANDS | Command Description |
|---|---|
| WAIT: {LF} | Wait for any one button to be pressed, then continue executing the script program. |
| COLLECT: device{LF} | Collect measurements from the monitoring device specified in the COLLECT command. The user is preferably prompted to connect the specified monitoring device to the apparatus and press a button to continue. |
| NUMBER: aaaa{LF} | Assign a script identification code to the script program. The script identification code from the most recently executed NUMBER statement is subsequently transmitted to the server along with the query responses and device measurements. The script identification code identifies to the server which script program was most recently executed by the remote apparatus. |
| DELAY: t{LF} | Wait until time t specified in the DELAY command, usually the prescribed connection time. |
| CONNECT: {LF} | Perform a connection routine to establish a communication link to the server, transmit the patient identification code, query responses, device measurements, and script identification code to the server, and receive and store a new script program. When the server instructs the apparatus to disconnect, the script interpreter is restarted, allowing the new script program to execute. |

The script commands illustrated in Table 1 are representative of the preferred embodiment and are not intended to limit the scope of the invention. After consideration of the ensuing description, it will be apparent to one skilled in the art many other suitable scripting languages and sets of script commands may be used to implement the invention.

The script generator 50 preferably stores a script program template which it uses to create each script program 40. To generate a script program 40, the script generator 50 inserts into the template the script information entered in the screen 56. For example, FIGS. 6A–6B illustrate a sample script program 40 created by the script generator 50 from the script information shown in FIG. 5.

The script program 40 includes display commands to display the queries and response choices entered in fields 94 and 96, respectively. The script program 40 also includes input commands to receive responses 42 to the queries. The script program 40 further includes a collect command to collect device measurements 44 from the monitoring device 28 specified in the check boxes 98. The script program 40 also includes commands to establish a subsequent communication link to the server 18 at the connection time specified in field 100 FIG. 5. The steps included in the script program 40 are also shown in the flow chart of FIGS. 12A–12B and will be discussed in the operation section below.

Referring again to FIG. 2, the script assignor 52 is used to assign script programs 40 to the patients. The script programs 40 are assigned in accordance with script assignment information entered through workstation 20. The script assignment information is entered through a script assignment screen 57, which is preferably implemented as a web page on the server 18.

Figure 7:
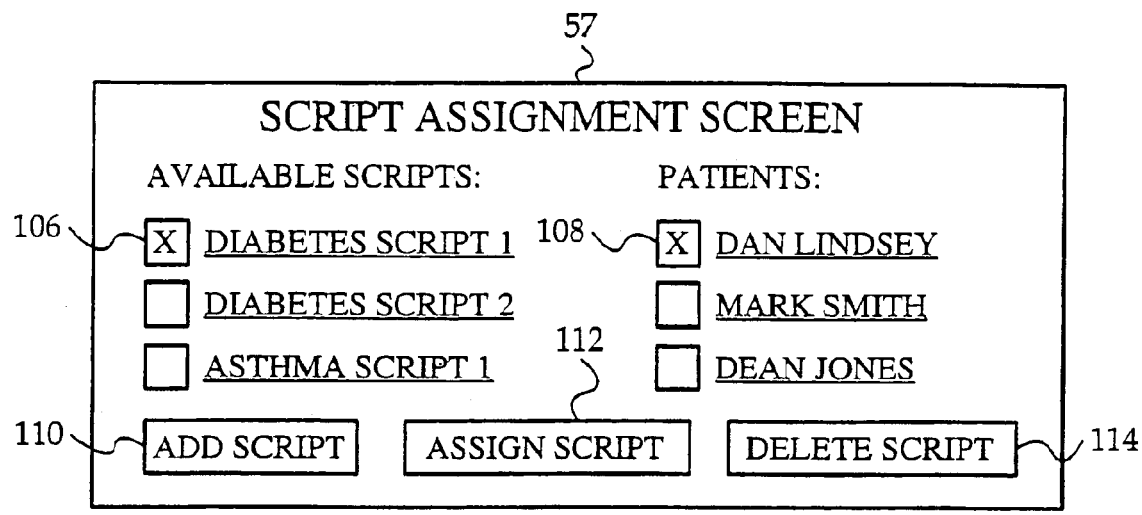
FIG. 7 is a script assignment screen according to the preferred embodiment of the invention

FIG. 7 illustrates a sample script assignment screen 57 as it appears on workstation 20. The screen 57 includes check boxes 106 for selecting a script program 40 to be assigned, and check boxes 108 for selecting the patients to whom the script program is to be assigned. The screen 57 also includes an ASSIGN SCRIPT button 112 for entering the assignments. When button 112 is pressed, the script assignor 52 creates and stores for each patient selected in check boxes 108 a respective pointer to the script program 40 selected in the check boxes 106. Each pointer is stored in the patient look-up table 46 of the database 38. The screen 57 further includes an ADD SCRIPT button 110 for accessing the script entry screen and a DELETE SCRIPT button 114 for deleting a script program 40.

Referring again to FIG. 2, the report generator 54 is designed to generate a patient report 58 from the responses 42 and the device measurements 44 received in the server 18. The patient report 58 is displayed on the workstation 20. FIG. 10 shows a sample patient report 58 produced by the report generator 54 for a selected patient. The patient report 58 includes a graph 116 of the device measurements 44 received from the patient, as well as a listing of the responses 42 received from the patient. Specific techniques for writing a report generator program to display data in this manner are well known in the art.

The operation of the preferred embodiment is illustrated in FIGS. 1–12. FIG. 11A is a flow chart illustrating steps included in the monitoring application executed by the server 18. FIG. 11B is a continuation of the flow chart of FIG. 11A. In step 202, the server 18 determines if new script information has been entered through the script entry screen 56. If new script information has not been entered, the server 18 proceeds to step 206. If new script information has been entered, the server 18 proceeds to step 204.

As shown in FIG. 5, the script information includes a set of queries, and for each of the queries, corresponding response choices. The script information also includes a selected monitoring device type from which to collect device measurements 44. The script information further includes a prescribed connection time for each apparatus to establish a subsequent communication link to the server 18. The script information is generally entered in the server 18 by a healthcare provider, such as the patients' physician or case manager. Of course, any person desiring to communicate with the patients may also be granted access to the server 18 to create and assign script programs 40. Further, it is to be understood that system 16 may include any number of remote interfaces for entering script generation and script assignment information in the server 18.

In step 204, the script generator 50 generates a script program from the information entered in the screen 56. The script program is stored in the database 38. Steps 202 and 204 are preferably repeated to generate multiple script programs, e.g. a script program for diabetes patients, a script program for asthma patients, etc. Each script program corresponds to a respective one of the sets of queries entered through the script entry screen 56. Following step 204, the server 18 proceeds to step 206.

In step 206, the server 18 determines if new script assignment information has been entered through the assignment screen 57. If new script assignment information has not been entered, the server 18 proceeds to step 210. If new script assignment information has been entered, the server 18 proceeds to step 208. As shown in FIG. 7, the script programs are assigned to each patient by selecting a script program through check boxes 106, selecting the patients to whom the selected script program is to be assigned through check boxes 108, and pressing the ASSIGN SCRIPT button 112. When button 112 is pressed, the script assignor 52 creates for each patient selected in the check boxes 108 a respective pointer to the script program selected in the check boxes 106. In step 208, each pointer is stored in the look-up table 46 of the database 38. Following step 208, the server 18 proceeds to step 210.

In step 210, the server 18 determines if any of the apparatuses are remotely connected to the server. Each patient to be monitored is preferably provided with his or her own remotely programmable apparatus, which has the patient's unique identification code, stored therein. Each patient is thus uniquely associated with a respective one of the apparatuses. If none of the apparatuses is connected, the server 18 proceeds to step 220. If an apparatus is connected, the server 18 receives from the apparatus the patient's unique identification code in step 212. In step 214, the server 18 receives from the apparatus 26 the query responses 42, device measurements 44, and script identification code recorded during execution of a previously assigned script program. The script identification code identifies to the server 18 which script program was executed by the apparatus to record the query responses 42 and device measurements 44. The responses, device measurements, and script identification code are stored in the database 38.

In step 216, the server 18 uses the patient identification code to retrieve from the table 46 the pointer to the script program assigned to the patient. The server 18 then retrieves the assigned script program from the database 38. In step 218, the server 18 transmits the assigned script program to the patient's remotely programmable apparatus through the communication network 24. Following step 218, the server 18 proceeds to step 220.

In step 220, the server 18 determines if a patient report request has been received from the workstation 20. If no report request has been received, the server 18 returns to step 202. If a report request has been received for a selected patient, the server 18 retrieves from the database 38 the measurements 44 and query responses 42 last received from the patient, step 222. In step 224, the server 18 generates and displays the patient report 58 on the the workstation 20. As shown in FIG. 10, the report 58 includes the device measurements 44 and query responses 42 last received from the patient. Following step 224, the server 18 returns to step 202.

Figure 12A:
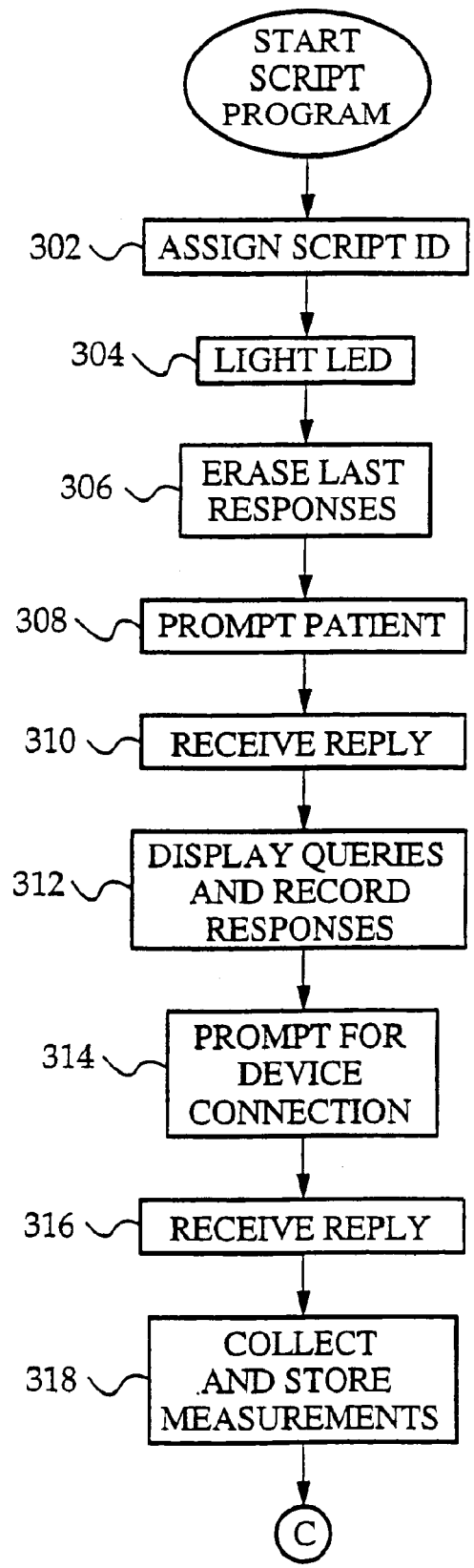
FIG. 12A is a flow chart illustrating the steps included in the script program of FIGS. 6A–6B.
Figure 12B:
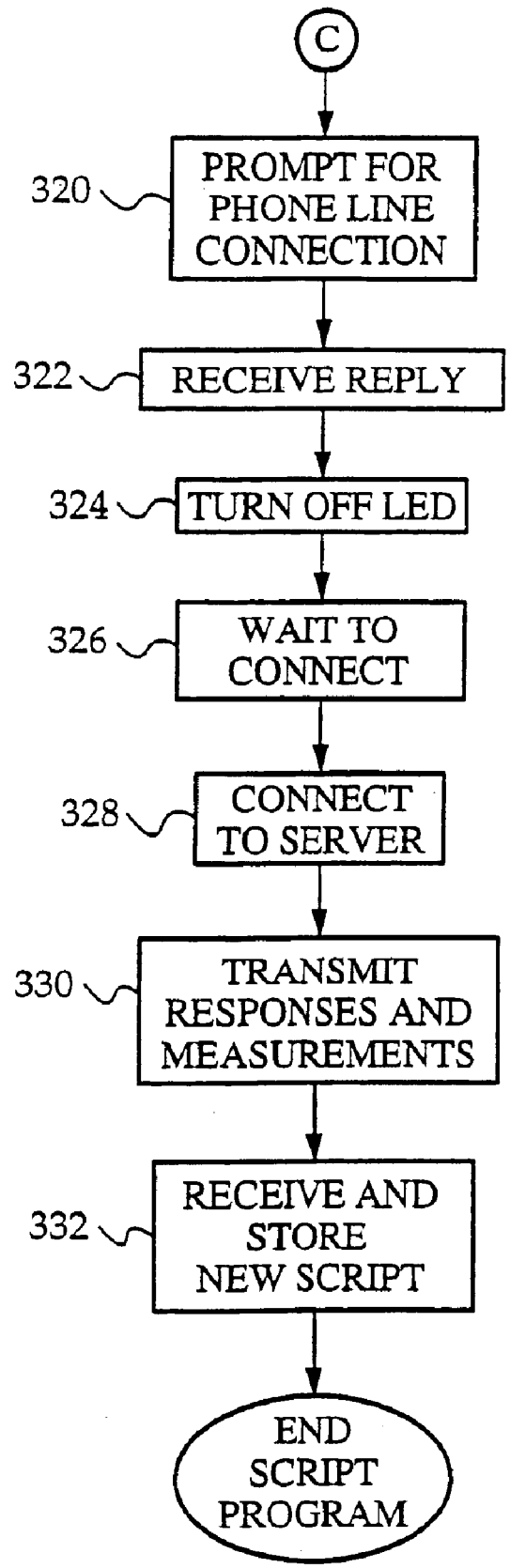
FIG. 12B is a continuation of the flow chart of FIG. 12.

FIGS. 12A–12B illustrate the steps included in the script program executed by the apparatus 26. Before the script program is received, the apparatus 26 is initially programmed with the patient's unique identification code and the script interpreter used by microprocessor 76 to execute the script program. The initial programming may be achieved during manufacture or during an initial connection to the server 18. Following initial programming, the apparatus 26 receives from the server 18 the script program assigned to the patient associated with the apparatus 26. The script program is received by the modem 86 through a first communication link and stored in the memory 80.

In step 302, microprocessor 76 assigns a script identification code to the script program and stores the script identification code in the memory 80. The script identification code is subsequently transmitted to the server 18 along with the query responses 42 and the device measurements 44 to identify to the server 18 which script program was most recently executed by apparatus 26. In step 304, the microprocessor 76 lights LED 74 to notify the patient that he or she has unanswered queries stored in the apparatus 26. The LED 74 preferably remains lit until the patient answers the queries. In step 306, the microprocessor 76 erases from the memory 80 the last set of query responses recorded.

In step 308, the microprocessor 76 prompts the patient by displaying on the display 64 "ANSWER QUERIES NOW? PRESS ANY BUTTON TO START". In step 310, the microprocessor 76 waits until a reply to the prompt is received from the patient. When a reply is received, the microprocessor 76 proceeds to step 312. In step 312, the microprocessor 76 executes successive display and input commands to display the queries and response choices on the display 64 and to receive responses to the queries.

Figure 8:
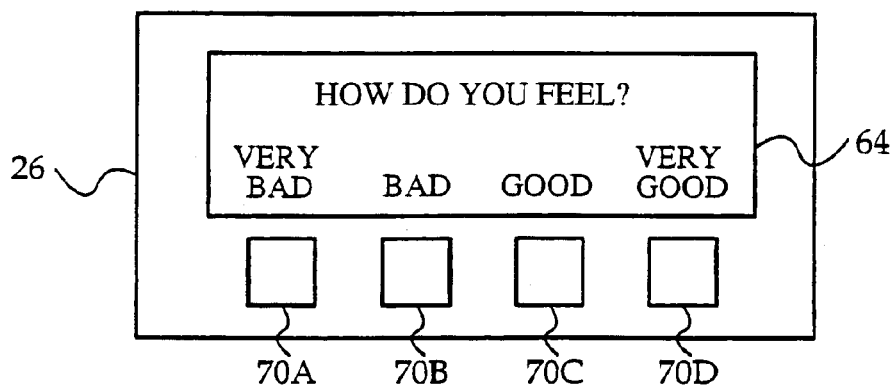
FIG. 8 is a sample query appearing on the apparatus of FIGS. 1A–D.

FIG. 8 illustrates a sample query and its corresponding response choices as they appear on the display 64 The response choices are positioned on the display 64 such that each response choice is located proximate a respective one of input buttons 70A–D. In the preferred embodiment, each response choice is displayed immediately above a respective input button 70A–D. The patient presses the button 70A–D corresponding to his or her response. The microprocessor 76 stores each response in the memory 80.

Figure 9:
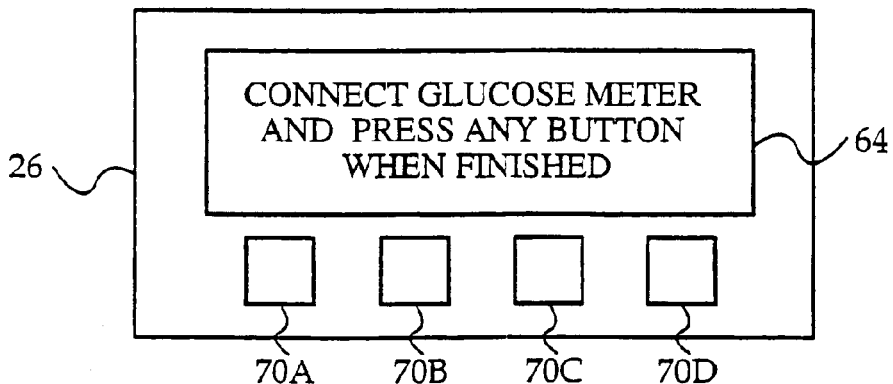
FIG. 9 is a sample prompt appearing on the display of the apparatus of FIG. 3.
Figure 11A:
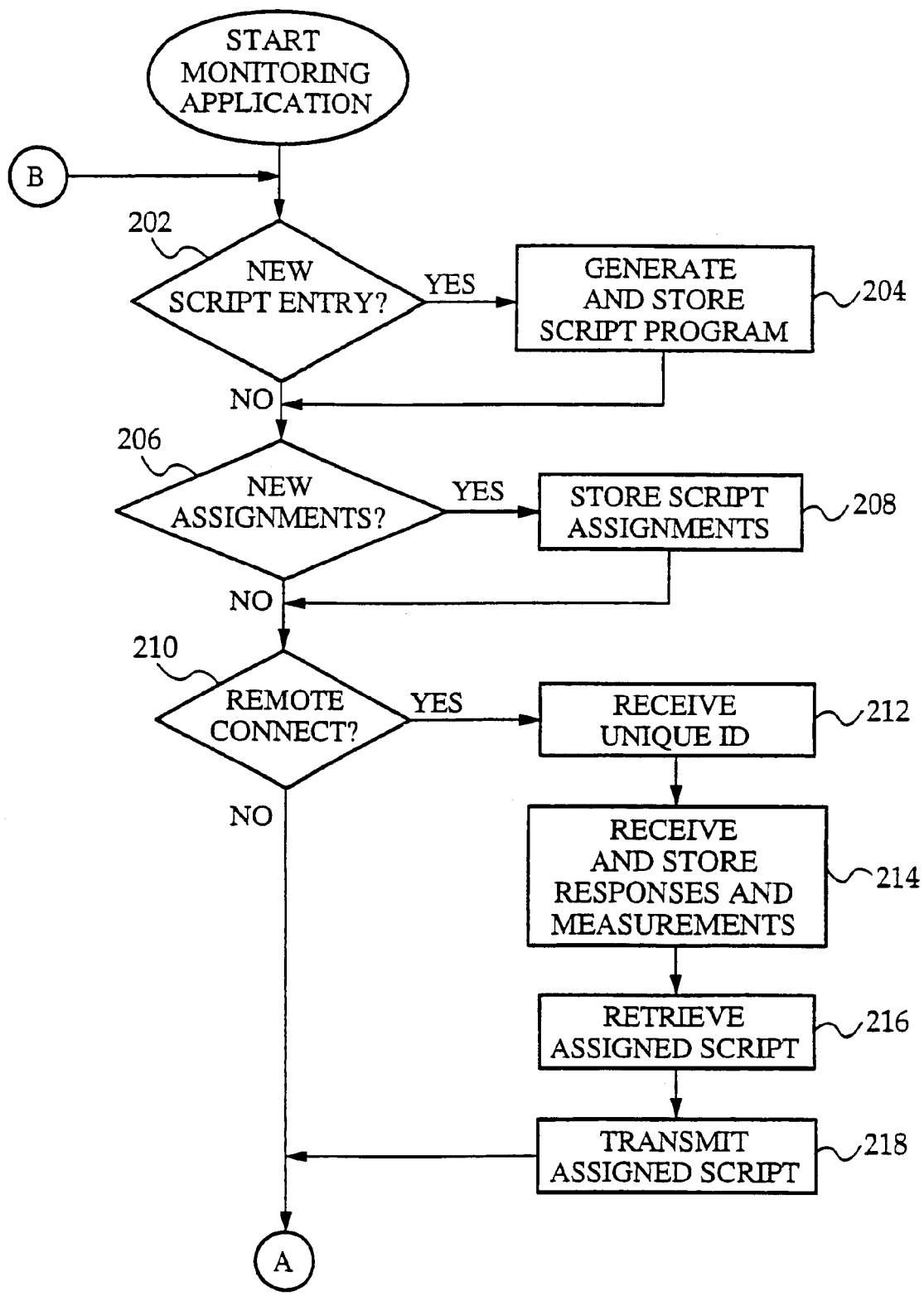
FIG. 11A is a flow chart illustrating the steps included in a monitoring application executed by the server of FIGS. 1A–D according to the present invention.
Figure 11B:
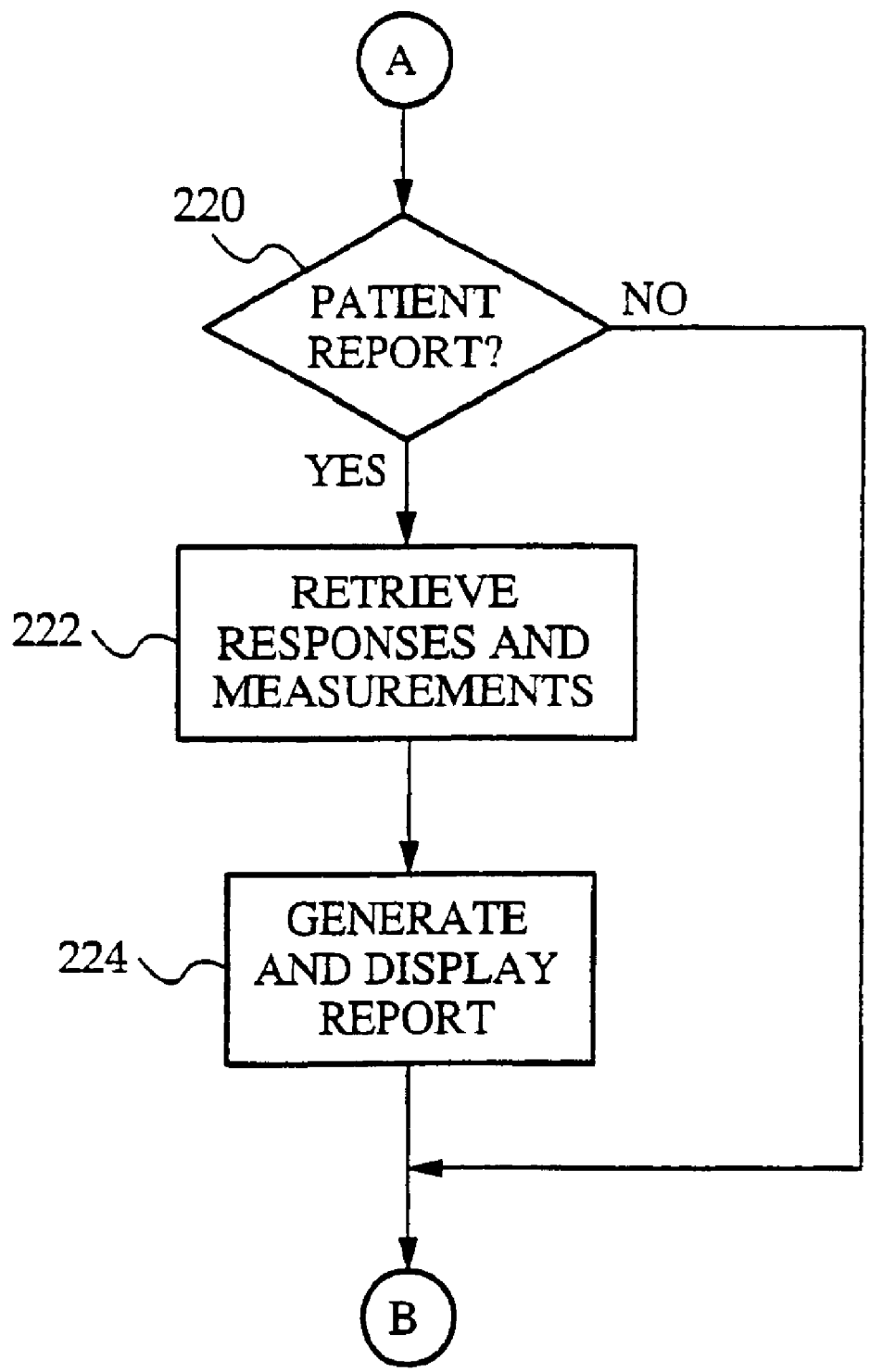
FIG. 11B is a continuation of the flow chart of FIG. 11A

In steps 314–318, the microprocessor 76 executes commands to collect the device measurements 44 from a selected the monitoring device 28. The script program specifies the selected monitoring device from which to collect the measurements. In step 314, the microprocessor 76 prompts the patient to connect the selected monitoring device 28, for example a blood glucose meter, to one of device jacks 68A–C. A sample prompt is shown in FIG. 9. In step 316, the microprocessor 76 waits until a reply to the prompt is received from the patient. When a reply is received, the microprocessor 76 proceeds to step 318. In step 318, the microprocessor 76 collects device measurements 44 from the monitoring device 28 through the interface 90. The measurements 44 are stored in the memory 80.

In step 320, the microprocessor 76 prompts the patient to connect the apparatus 26 to the telephone jack 22 so that the apparatus 26 may connect to the server 18 at the prescribed connection time. In step 322, the microprocessor 76 waits until a reply to the prompt is received from the patient. When a reply is received, the microprocessor 76 turns off the LED 74 in step 324. In step 326, the microprocessor 76 waits until it is time to connect to the server 18. The microprocessor 76 compares the connection time specified in the script program to the current time output by the clock 84.

In step 328, the microprocessor 76 establishes a subsequent communication link between the apparatus 26 and the server 18 through the modem 86 and the communication network 24. If the connection fails for any reason, the microprocessor 76 repeats step 328 to get a successful connection. In step 330, the microprocessor 76 transmits the device measurements 44, query responses 42, script identification code, and patient identification code stored in the memory 80 to the server 18 through the subsequent communication link. In step 332, the microprocessor 76 receives through the communication network 24 a new script program from the server 18. The new script program is stored in the memory 80 for subsequent execution by the microprocessor 76. Following step 332, the script program ends.

One advantage of the monitoring system of the present invention is that it allows each patient to select a convenient time to respond to the queries, so that the monitoring system is not intrusive to the patient's schedule. A second advantage of the monitoring system is that it incurs very low communications charges because each remote apparatus connects to the server 18 at times when communication rates are lowest. Moreover, the cost to manufacture each remote the apparatus 26 is very low compared to personal computers or internet terminals, so that the monitoring system is highly affordable.

A third advantage of the monitoring system is that it allows each apparatus 26 to be programmed remotely through script programs 40. Patient surveys, connection times, display prompts, selected monitoring devices, patient customization, and other operational details of each apparatus 26 may be easily changed by transmitting a new script program 40 to apparatus 26. Moreover, each script program 40 may be easily created and assigned by remotely accessing the server 18 through the Internet. Thus, the invention provides a powerful, convenient, and inexpensive system for remotely monitoring a large number of patients.

Figure 13:
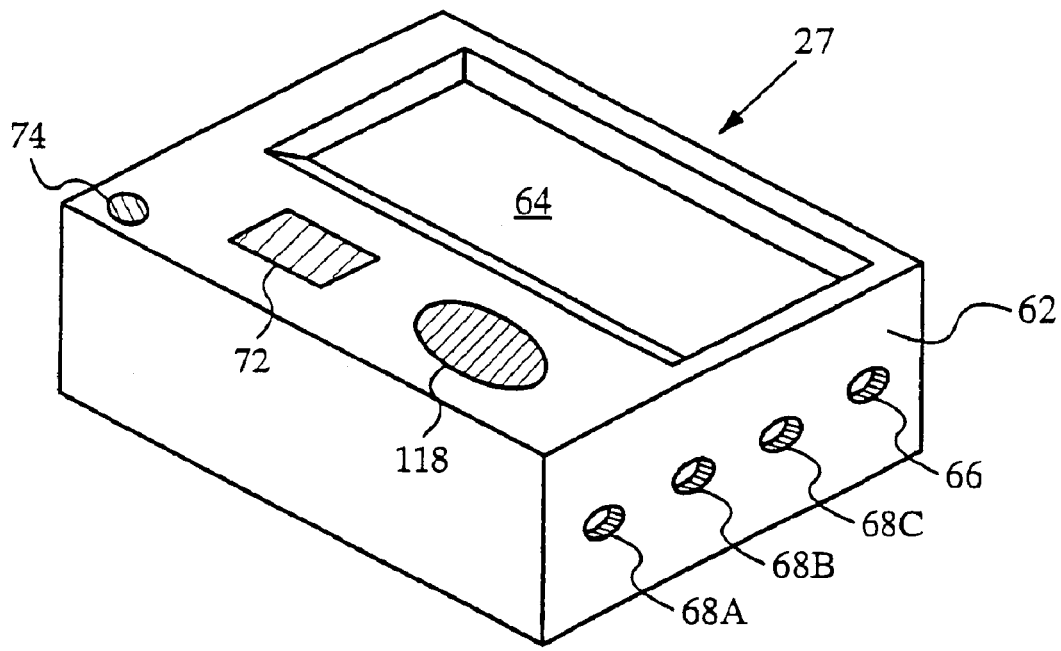
FIG. 13 is a perspective view of a remotely programmable apparatus according to an embodiment of the present invention.
Figure 14:
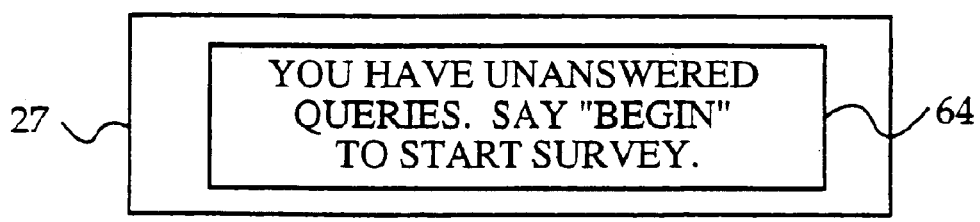
FIG. 14 is a sample prompt appearing on a display of the apparatus of FIG. 13.
Figure 15:
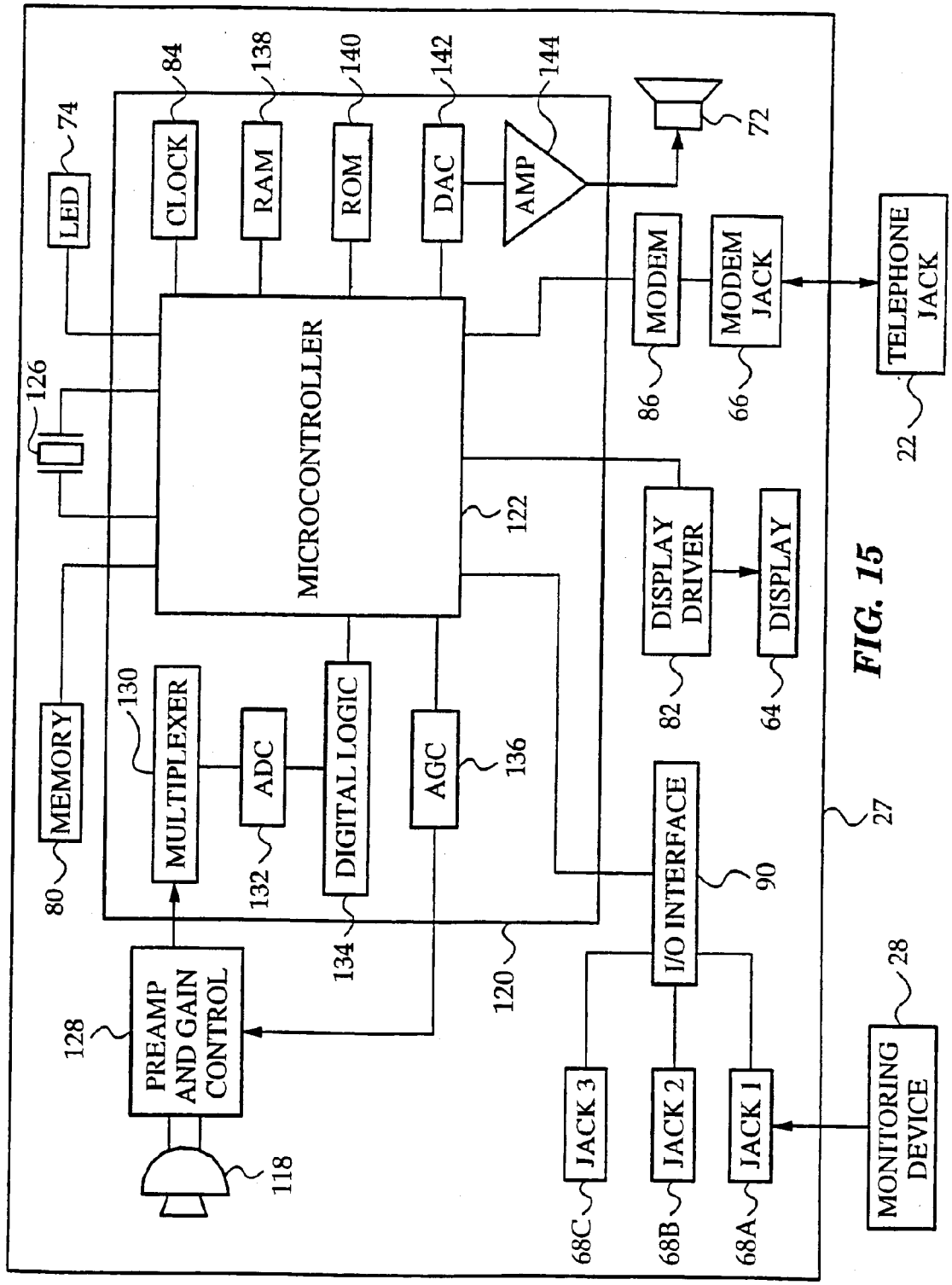
FIG. 15 is a block diagram illustrating the components of the apparatus of FIG. 13.

FIGS. 13–15 illustrate a second embodiment of the invention in which each remotely programmable apparatus includes all of the functionality of the first embodiment described above while also including speech recognition and speech synthesis functionality. FIG. 13 shows a perspective view of the remotely programmable apparatus 27 according to the second embodiment. The apparatus 27 includes a speaker 72 for audibly communicating queries and prompts to the patient. The apparatus 27 also includes a microphone 118 for receiving spoken responses to the queries and prompts. The apparatus 27 may optionally include a display 64 for displaying prompts to the patient, as shown in FIG. 14.

FIG. 15 is a schematic block diagram illustrating the components of the apparatus 27 in greater detail. The apparatus 27 is similar in design to the apparatus 26 of the preferred embodiment except that the apparatus 27 includes an audio processor chip 120 in place of the microprocessor 76. The audio processor chip 120 is preferably an RSC-164 chip commercially available from Sensory Circuits Inc. of 1735 N. First Street, San Jose, Calif. 95112.

The audio processor chip 120 has a microcontroller 122 for executing script programs received from the server 18. A memory 80 is connected to the microcontroller 122. Memory 80 stores the script programs and a script interpreter used by the microcontroller 122 to execute the script programs. The memory 80 also stores measurements received from the monitoring device 28, responses to the queries, script identification codes, and the patient's unique identification code.

The audio processor chip 120 also has built in speech synthesis functionality for synthesizing queries and prompts to a patient through the speaker 72. For speech synthesis, the chip 120 includes a digital to analog converter (DAC) 142 and an amplifier 144. The DAC 142 and the amplifier 144 drive the speaker 72 under the control of the microcontroller 122.

The audio processor chip 120 further has built in speech recognition functionality for recognizing responses spoken into the microphone 118. Audio signals received through the microphone 118 are converted to electrical signals and sent to a preamp and gain control circuit 128. The preamp and gain control circuit 128 is controlled by an automatic gain control circuit 136, which is in turn controlled by the microcontroller 122. After being amplified by the preamp 128, the electrical signals enter the chip 120 and pass through a multiplexer 130 and an analog to digital converter (ADC) 132. The resulting digital signals pass through a digital logic circuit 134 and enter microcontroller 122 for speech recognition.

The audio processor chip 120 also includes a RAM 138 for short-term memory storage and a ROM 140, which stores programs executed by the microcontroller 122 to perform speech recognition and speech synthesis. The chip 120 operates at a clock speed determined by a crystal 126. The chip 120 also includes a clock 84 that provides the current date and time to the microcontroller 122. As in the preferred embodiment, the apparatus 27 includes an LED 74, display driver 82, modem 86, and device interface 90, all of which are connected to the microcontroller 122.

The operation of the second embodiment is similar to the operation of the preferred embodiment except that queries, response choices, and prompts are audibly communicated to the patient through the speaker 72 rather than being displayed to the patient on the display 64. The operation of the second embodiment also differs from the operation of the preferred embodiment in that responses to the queries and prompts are received through the microphone 118 rather than through user input buttons.

The script programs of the second embodiment are similar to the script program shown in FIGS. 6A–6B, except that each display command is replaced by a speech synthesis command and each input command is replaced by a speech recognition command. The speech synthesis commands are executed by the microcontroller 122 to synthesize the queries, response choices, and prompts through speaker 72. The speech recognition commands are executed by the microcontroller 122 to recognize responses spoken into microphone 118.

For example, to ask the patient how he or she feels and record a response, the microcontroller 122 first executes a speech synthesis command to synthesize through the speaker 72 "How do you feel? Please answer with one of the following responses: very bad, bad, good, or very good." Next, the microcontroller 122 executes a speech recognition command to recognize the response spoken into the microphone 118. The recognized response is stored in the memory 80 and subsequently transmitted to the server. Other than the differences described, the operation and advantages of the second embodiment are the same as the operation and advantages of the preferred embodiment described above.

Although the first and second embodiments focus on querying individuals and collecting responses to the queries, the system of the invention is not limited to querying applications. The system may also be used simply to communicate messages to the individuals. FIGS. 16–19 illustrate a third embodiment in which the system is used to perform this automated messaging function. In the third embodiment, each script program contains a set of statements to be communicated to an individual rather than a set of queries to be answered by the individual. Of course, it will be apparent to one skilled in the art that the script programs may optionally include both queries and statements.

Figure 16:
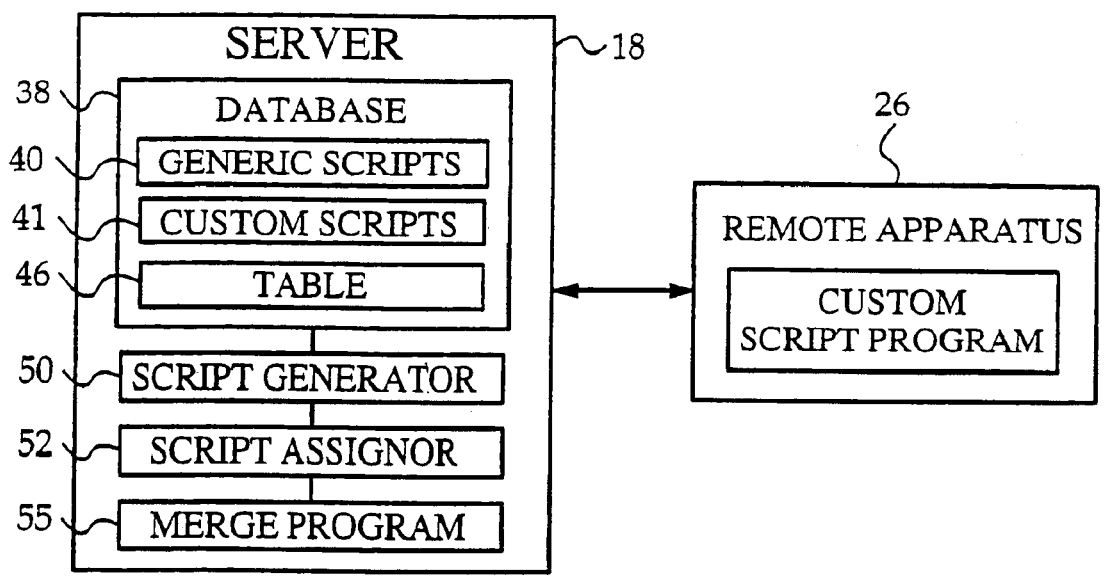
FIG. 16 is a schematic block diagram illustrating the interaction of the server of FIGS. 1A–D with the apparatus of FIG. 3 according to another embodiment of the present invention.

The third embodiment also shows how the queries and statements may be customized to each individual by merging personal data with the script programs, much like a standard mail merge application. As mentioned above, the individual may be identified for selection of individualized information either through an individual identification code associated with the remote apparatus 26 and stored in memory 80. Referring to FIG. 16, personal data relating to each individual is preferably stored in the look-up table 46 of the database 38. By way of example, the data may include each individual's name, the name of each individual's physician, test results, appointment dates, or any other desired data. As in the preferred embodiment, the database 38 also stores generic script programs 40 created by the script generator 50.

Figure 17:
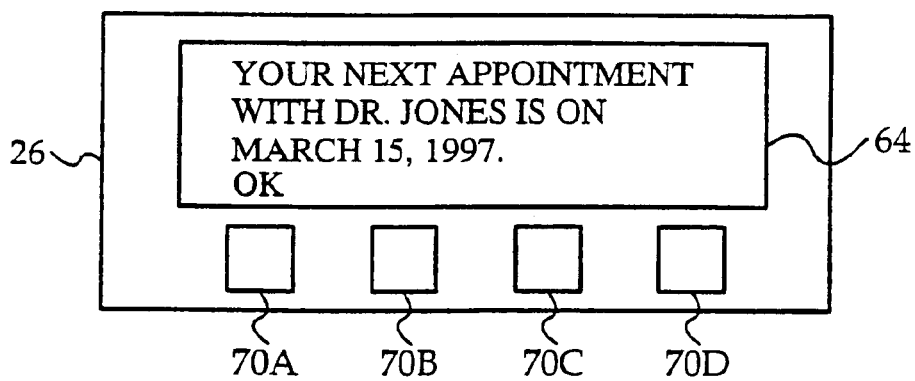
FIG. 17 is a first sample message appearing on the display of the apparatus of FIG. 3.
Figure 18:
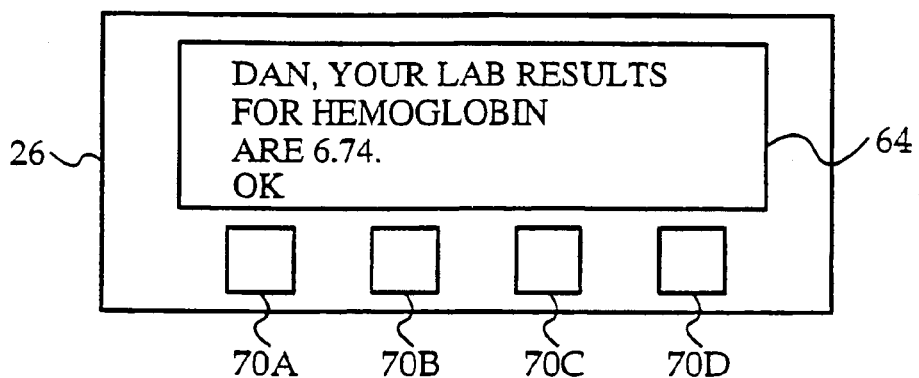
FIG. 18 is a second sample message appearing on the display of the apparatus of FIG. 3.

The server 18 includes a data merge program 55 for merging the data stored in table 46 with generic script programs 40. The data merge program 55 is designed to retrieve selected data from table 46 and to insert the data into statements in generic script programs 40, thus creating custom script programs 41. Each custom script program 41 contains statements that are customized to an individual. For example, the statements may be customized with the individual's name, test results, etc. Examples of such customized statements are shown in FIGS. 17–18.

The operation of the third embodiment is similar to the operation of the preferred embodiment except that the script programs are used to communicate messages to the individuals rather than to query the individuals. Each message is preferably a set of statements. Referring to FIG. 19, the statements may be entered in the server 18 through the script entry screen 56, just like the queries of the preferred embodiment.

Each statement preferably includes one or more insert commands specifying data from table 46 to be inserted into the statement. The insert commands instruct the data merge program 55 to retrieve the specified data from the database 38 and to insert the data into the statement. For example, the insert commands shown in FIG. 19 instruct the data merge program 55 to insert a physician name, an appointment date, a patient name, and a test result into the statements. As in the preferred embodiment, each statement may also include one or more response choices, which are entered in fields 96.

Following entry of the statements and response choices, CREATE SCRIPT button 102 is pressed. When the button 102 is pressed, the script generator 50 generates a generic script program from the information entered in the screen 56. The generic script program is similar to the script program shown in FIGS. 6A–6B, except that the display commands specify statements to be displayed rather than queries. Further, the statements include insert commands specifying data to be inserted into the script program. As in the preferred embodiment, multiple script programs are preferably generated, e.g. a generic script program for diabetes patients, a generic script program for asthma patients, etc. The generic script programs are stored in the database 38.

Following generation of the generic script programs, the server 18 receives script assignment information entered through the script assignment screen 57. As shown in FIG. 7, the script programs are assigned by first selecting one of the generic script programs through the check boxes 106, selecting individuals through the check boxes 108, and pressing the ASSIGN SCRIPT button 112. When the button 112 is pressed, the data merge program 55 creates a custom script program 41 for each individual selected in check boxes 108.

Each custom script program 41 is preferably created by using the selected generic script program as a template. For each individual selected, the data merge program 55 retrieves from the database 38 the data specified in the insert commands. Next, the data merge program 55 inserts the data into the appropriate statements in the generic script program 40 to create a custom script program 41 for the individual. Each custom script program 41 is stored in the database 38.

As each custom script program 41 is generated for an individual, the script assignor 52 assigns the script program 41 to the individual. This is preferably accomplished by creating a pointer to the custom script program and storing the pointer with the individual's unique identification code in the table 46. When the individual's remotely programmable apparatus connects to the server 18, the server 18 receives from the remotely programmable apparatus 26 the individual's unique identification code. The server 18 uses the unique identification code to retrieve from the table 46 the pointer to the custom script program assigned to the individual. Next, the server 18 retrieves the assigned script program from the database 38 and transmits the script program to the individual's remotely programmable apparatus 26 through the communication network 24.

The apparatus receives and executes the script program. The execution of the script program is similar to the execution described in the preferred embodiment, except that statements are displayed to the individual rather than queries. FIGS. 17–18 illustrate two sample statements as they appear on the display 64. Each statement includes a response choice, preferably an acknowledgment such as "OK". After reading a statement, the individual presses the button 70A–D corresponding to the response choice to proceed to the next statement. Alternatively, the script program may specify a period of time that each statement is to be displayed before proceeding to the next statement. The remaining operation of the third embodiment is analogous to the operation of the preferred embodiment described above.

Although it is presently preferred to generate a custom script program 41 for each individual as soon as script assignment information is received for the individual, it is also possible to wait until the individual's apparatus 26 connects to the server 18 before generating the custom script program 41. This is accomplished by creating and storing a pointer to the generic script program 40 assigned to the individual, as previously described in the preferred embodiment. When the individual's apparatus 26 connects to the server 18, the data merge program 55 creates a custom script program 41 for the individual from the generic script program 40 assigned to the individual. The custom script program 41 is then sent to the individual's apparatus 26 for execution.

Alternate Embodiments

In an alternate embodiment, when the user or patient (the terms user and patient are used interactively) activates the user input button 70E (hereinafter the red button) a command signal is sent to the processor 76. The processor 76 dial a preset phone number according to the command signal. The preset phone number is that of an answering service at the server 18 or at a workstation 20. The answering service identifies the patient or user associated with the remote apparatus 26 that generated the call based on an identifier sent with the call and user information stored in memory in the database (similar to caller ID). The system (server 18 or workstation 20) that receives the call then retrieves patient information with previous patient/user responses stored at the server's database 38, within memory at the workstation 20, or at some other remotely located storage site. The retrieved patient information is displayed to a live person who is in telephonic communication with the patient. This allows the patient to be placed in immediate contact with a person who has displayed before them the patient's personal health information or other patient historical information. The person receiving the call provides effective communication with the patient, because of the ability to view pertinent information.

In an alternate embodiment, an automated answering service is the recipient of the call made by the remote apparatus 26. The automated answering service asks a series of questions according to the retrieved patient information in order to triage the patient toward different actions depending upon the situation. The patient information also includes previous patient interactions with the automated answering service.

The system receiving the call process patient responses according to the content associated with the question asked. Content is one of the following categories: symptoms; behavior; knowledge. The categories include such things as requests for service or product orders. In one example, the automated answering service asks "do you have difficulty breathing? press the red button if you are." If the patient then presses the red button, the call is forwarded to a case manager or a nurse on call.

In another example, red button selection is associated with a request for service. When the red button is pressed, the automated answering service asks "do you need someone to change your bed? press the red button if yes." If the patient presses the red button, a home care agency coordinating ancillary daily activity services is notified or is forwarded the call. Other service companies, such as transport companies or concierge service companies, are other possible recipients of forwarded calls depending what actions are available to the patients.

The automated answering service is dynamically adaptable based on previous interactions with the automated answering service. For example, the past couple of times the patient activated the red button and answered the question(s), the patient was connected to an emergency health care worker. If the worker determined through review questions of the patient's present condition, maybe information generated by the monitoring device sent over the network 24 to a workstation operated by the worker, and retrieved patient information that no emergency existed, the worker records this situation into the patient's records. If the patient's record includes a number of false alarms that exceed a predetermined limit over a period of time, the automated answering service reprograms itself so that the next time the patient activates the red button the patient is directly connected to a live person that is designated for non-emergency patient interaction or to other questions that direct the patient to the person designated for non-emergency patient interaction. This frees-up emergency healthcare workers from dealing with someone who has a history of not needing their expertise.

Figure 20:
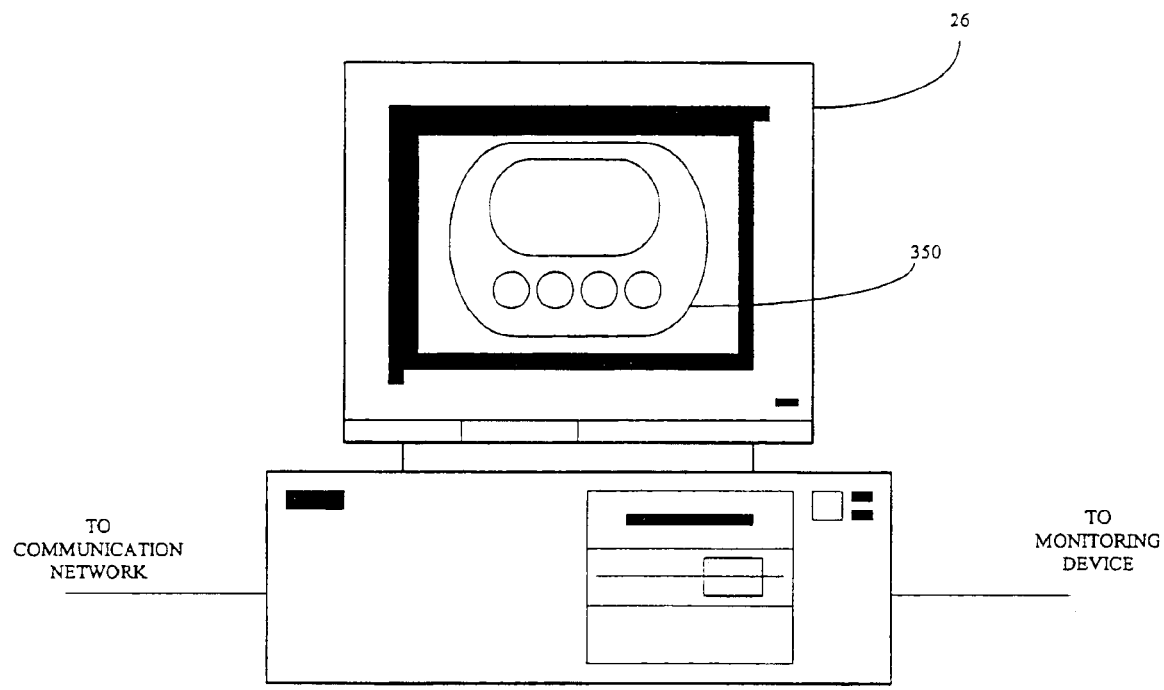
FIGS. 20 and 21 are block diagrams of alternate embodiments of the present invention.
Figure 21:
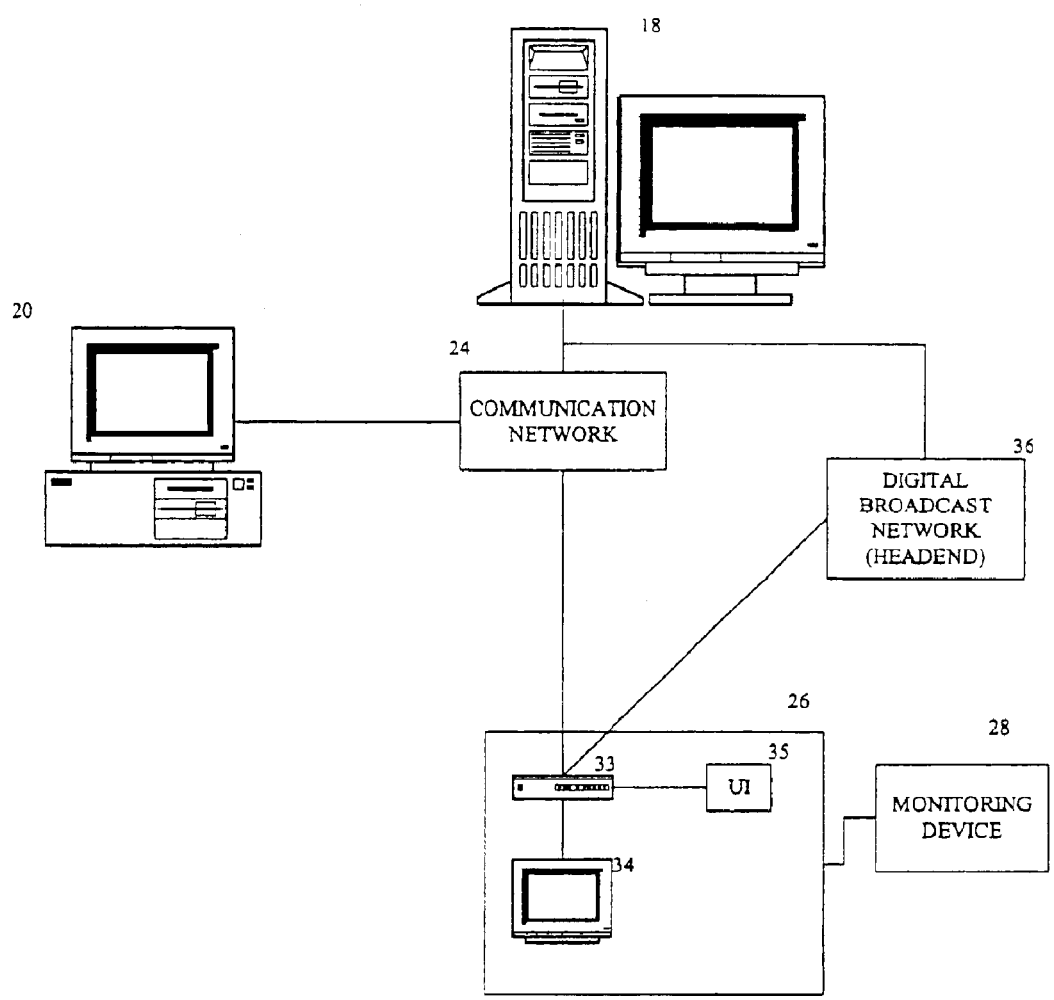

FIGS. 20 and 21 illustrate alternate embodiments of the invention illustrated in FIG. 1. In FIG. 20, the remote apparatus 26 is a personal computer including a processor and a user interface, e.g. display, keyboard, mouse, or other input and output devices (not all shown), that receives the script program, processes the script program and presents the script program for user interaction. For example, the script program requires that the personal computer present an image of a stand-alone remote apparatus 350, such as the Health Buddy™ produced by Health Hero Network, Inc., on the display. The user then interacts with the displayed image of the stand-alone remote apparatus by operating the user interface(s) of the personal computer to select displayed responses. The displayed image of the stand-alone remote apparatus presents a virtual image with the same functionality as the apparatuses 26 and 27, as described above in FIGS. 3 and 13. It can be appreciated to those of ordinary skill in the art that the system of FIG. 20 provides all or part of the functionality of the apparatuses shown in FIGS. 3 and 13, but does it on a personal computer.

FIG. 21 includes all the components of the FIG. 1 and a digital television network 36 in communication with the server 18 and the remote apparatus 26. The remote apparatus 26 of FIG. 21 is an interactive television system that includes a processing unit 33, such as a satellite broadcast receiving, set-top processor with OpenTV signal processing software, a display 34, such as a television set, and a user interface 35, such as a remote control.

The remote apparatus 26, through the processing unit 33, is coupled to the communication network 24, the digital television network 36 and the monitoring device 28.

The processing unit 33 includes a CPU, memory and embedded software for receiving and processing both digital entertainment and advertisement content and digital script programs. Also, the processing unit 33 allows the user to view the entertainment and advertisement content, such as television programming, and interact with (i.e. respond to) the script programs. The script program(s) sent from the server 18 are viewable on the display 34 as they would appear on the display 64 of apparatus 26 or are viewed on a portion of the display 34. For example, the question with options shown in FIG. 8 would appear on the display 34. The user makes a selection of one of the choices by using the user interface 35, i.e. giving voice commands that are processed by a voice recognition system, controlling and activating a cursor, etc. Example methods of making a selection are to control a cursor icon on the display screen of the display 34 and activate the cursor icon when it is co-located with one of the choices, to assign different keyboard keys are designated as a different one of the displayed choices. Another method is to have the user interface include voice actuation software for processing user voice commands that request selection of a desired choice.

With respect to this invention, a "broadcast" includes any form of delivering the content from a source to many viewers, including transmission over the airwaves or via cable, the Internet, a closed-circuit network, or other means of communication. A "broadcast" does not require multiple persons to watch at once, but rather can include multiple individual and independent viewings, such as in the form of video on demand or access to web pages. Moreover, the term "broadcast" may include a single tailored transmission from a source to a single intended viewer. Accordingly, while a "broadcast" may include a transmission from one point to multiple recipients, it is not limited to that case. Likewise, with respect to this invention, a "broadcast" is "transmitted" in any of the above forms.

The processing unit 33 is a multimedia processor that receives transmitted broadcast programs from a digital broadcast network 36 via a communication link, such as a satellite or cable link. The processing unit 33 also transmits as well as receives data via the communication network 24. In addition, the multimedia processor has expansion ports to support additional user interface and other devices, such as keyboards, joysticks, trackballs, and to accept add-on circuits for enhanced sound, video, or processing performance.

Figure 22:
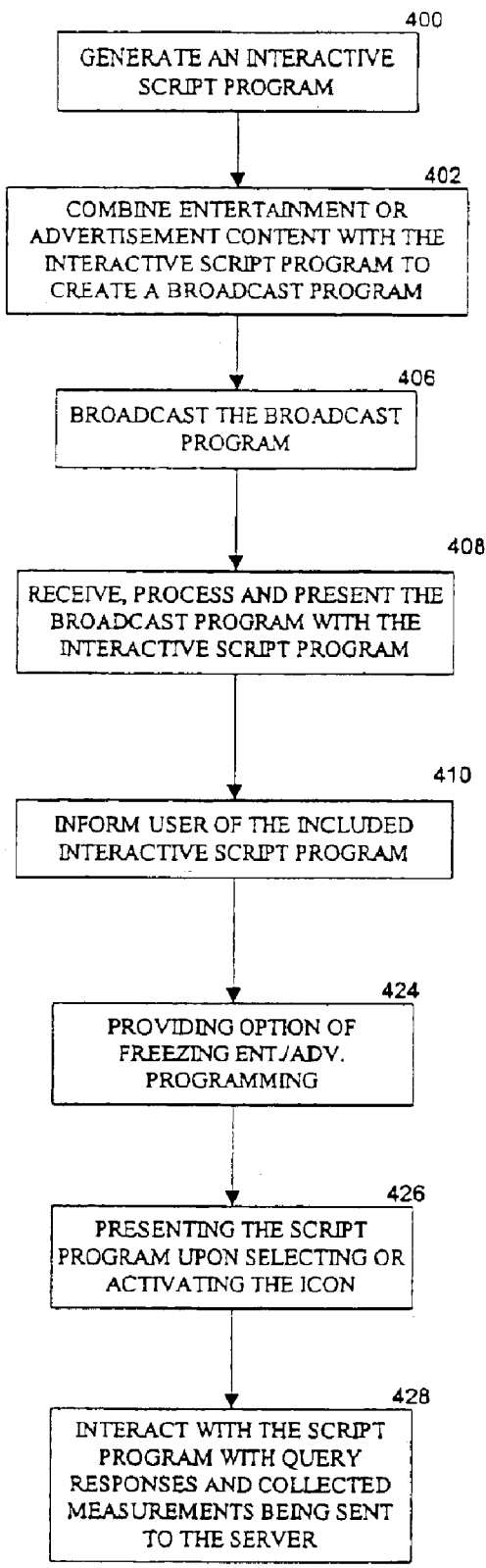
FIG. 22 is a flow chart illustrating the process performed by the system of FIGS. 21.

FIG. 22 is an example for illustrative purposes only of a method for increasing user use of script programs by allowing the user to quickly access the script program during viewing of an entertainment or advertisement program in an interactive TV system. FIG. 22 illustrates a process performed by the system shown in FIG. 21. At block 400, the server 18 generates an interactive script program. In an alternate embodiment, the script program is fully or partially created at another remotely coupled computer, such as workstation 20, and added to multimedia content, then the script program and multimedia content is sent to the server 18 In one embodiment, the script program is specialized for a specific user according to a health care professional request or to a predefined health regimen based on user profile information. In an alternate embodiment the script program is generated in relation to entertainment or advertisement content that it will later be broadcasted with. Next, at block 402, the generated script program is combined with digital produced entertainment or advertisement content, i.e. a multimedia presentation, to create digital broadcast programming. The digital broadcast programming is then broadcasted or transmitted over the chosen communication link, block 406. At block 408, the processing unit 33 receives and processes the digital broadcast programming then presents the entertainment or advertisement content and the script program. The processing unit 33 as directed by software instructions previously imbedded in the processing unit 33, included with the digital broadcast programming or a combination of both processes the digital broadcast programming by determining its content and how that content is to be presented on the display 34. For example, the processing unit 33 determines if the script program is to be referenced by an icon over the entertainment content or displayed on a portion of the display with the entertainment content. As part of the presentation from block 408 the user is informed of any script program included in the broadcast programming, block 410. Then, at block 426, the user is presented with the script program after the user selects or activates the indication, e.g. an icon. Lastly, at block 428, the user interacts with the script program by responding to any queries and inputting any requested measurements or other responses. The interaction with the script program is similar to that described above for the system of FIG. 1. In another embodiment, the script program is presented in conjunction with the entertainment or advertisement content without requiring the user to select or activate an indicator.

Figure 23:
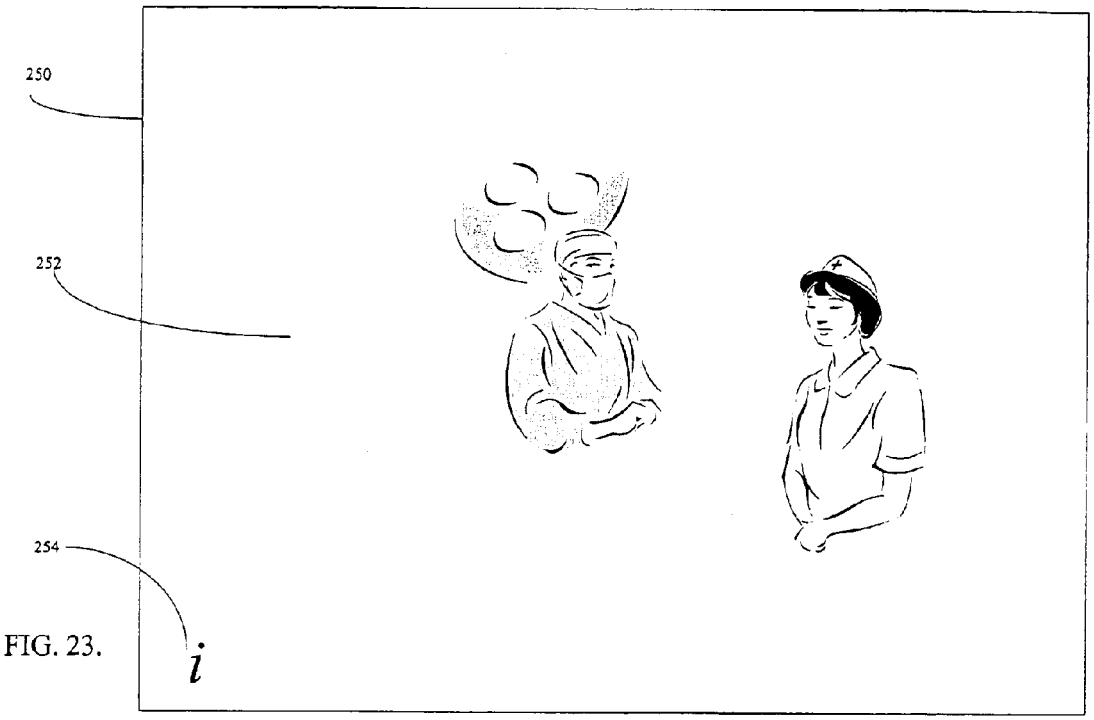
FIGS. 23 and 24 are example broadcast programming presentations with an included script program.
Figure 24:

FIGS. 23 and 24 are example images presented on the displays 34 in the system illustrated in FIG. 22. FIG. 23 illustrates a screen shot of a broadcast program 250 that includes entertainment content 252, such as a video program on heart surgery, and an icon 254. The icon 254 indicates that a script program is available for the viewer. In order for the viewer to access the script program, the viewer selects the icon 254. The program broadcasted from the broadcast network 24 may have included an entire script program or just a portion of a script program. If the entire script program were included with the broadcast, selection of the icon 254 would begin execution of the script program that was received. However, if only a portion of the script program was received and, for example, that portion only required that the icon 254 be displayed with the entertainment content 252, selection of the icon 254 sends a signal through a back channel, i.e. the link to the communication network 24, to the server 18. The sent signal is a request for the rest of or just more of the script program to be sent to the apparatus 26 either through broadcast network 36 or communication network 24.

FIG. 23 illustrates a screen shot of a broadcast program 250 that includes entertainment content 252 and a section that presents a script program image 256. In this example the viewer can interact with the script program image 256 while simultaneously viewing the entertainment content 252. As in FIG. 22 above, the script program may be fully or partially received and processed by the processing unit 33. And again, if it has only been partially received, viewer interaction at a predetermined spot in the displayed interaction process automatically initiates a request through the back channel to the server 18 for the rest of the script program.

Because the broadcast program 250 is a digital broadcast, it can be readily appreciated by those of ordinary skill in the art of digital interactive television, that the entertainment content may be paused until viewer completion of the script program. The script program which can be sent with an initial broadcast program or during presentation of a previously delivered broadcast program that is being presented on the display may also include instructions to pause the entertainment content until viewer completion of the script program at which time the entertainment program resumes. For example, the viewer's/patient's doctor creates a message at the workstation 20 requesting that the patient as soon as possible send blood pressure measurement readings. This message is generated as a new script program at the server 18. The server 18 then sends the new script program to the broadcast network 36. The broadcast network 36 includes hardware and/or software mechanisms for saving the new script program for inclusion with the next patient requested entertainment or advertisement content to be sent to the patient in the case where the patient is not presently viewing a broadcast from the broadcast network 36 or for just broadcasting the script program alone. If the patient is presently viewing entertainment or advertisement content received from the broadcast network 36, the new script program is received, processed and presented to the patient by the apparatus 26. The received new script program may include instructions to pause the presently viewed entertainment or advertisement content.

If the script program is specified for a particular patient, the server 18 or broadcast network 36 encodes the script program for that patient. The apparatus of that patient includes a decoding component within the processing unit 33 for decoding the encoded script program received with the broadcast program. For example, the script program includes a weight history chart of the patient. The present invention wants only the patient corresponding to this weight history chart to have viewing access. Therefore, it is encoded for transmission and encoded only by the corresponding patient's apparatus 26.

It can be appreciated to one of ordinary skill in the art that this decision, as with the other flow diagram decisions, can be an inherent decision in the processing of the received entertainment/advertisement programming and script program.

The embodiments of FIGS. 20 and 21 may also be implemented without any entertainment or advertisement content and perform the functions as to those that illustrated and described for FIG. 1.

The script programs or entertainment/advertisement programming can be designed for education and training of users. For example, the script program or information content could show a user, such as a patient, how to effectively use a medical treatment device. Also, the script program or information content could describe to users, such as doctors, nurses or anyone other professional, different treatment styles, plans or new medication.

A wide variety of information may be collected, delivered and analyzed in accordance with the present invention. For example, abandoned U.S. patent application Ser. No. 09/378,188 which is a continuation of U.S. Pat. No. 5,985,559, and unassigned U.S. patent application which is a continuation of U.S. patent application Ser. No. 09/041,809 (the text of which are hereby incorporated by reference) discusses information related to disease causes, treatments, and cures. Script programs include a set of queries for requesting data on lifestyle, environment, behavior, drug compliance, drug response over time, and other aspects. This data is then analyzed to identify trends and establish subgroups with similar responses.

Individuals' behavioral and environmental information in conjunction with their gene sequence information is analyzed to find drug candidates and drug targets. Individuals previously designated as having a high risk for developing a particular disease are each given an apparatus 26. Queries related to the individuals' behavior and environment are included in a script program sent from a server 18 to the apparatus 26 or from a server 18 to the apparatus 26 through a broadcast network 36. The individuals' responses are sent back to the server 18. The process of collecting individuals' information can take place over a long period of time to ensure accurate data and to allow researchers to observe progression of the disease. A data mining program on the server analyzes the individuals' behavioral and environmental information, as well as their gene sequence information. Differences in gene sequence information, or in behavioral and environmental factors between individuals who show a severe disease phenotype and those who show a mild severe disease phenotype can then be distinguished and used to develop new drug candidates, targets, or general treatments.

Genetic testing allows an individual to determine whether or not he or she has a predisposition to a certain disease. The degree of expressivity of a certain disease will be determined in part by an individual's environment and lifestyle. The environment and lifestyle information is retrieved from responses to queries sent from the server 18 to the apparatus 26 or from the server 18 to the apparatus 26 through the broadcast network 36. The present invention interprets a patient's gene sequence information and his or her environment and lifestyle to come up with a personalized prognosis. This procedure can be repeated many times over the course of a disease state to monitor a patient's condition. In addition, disease-causing pathogens can also have their genes sequenced. Using these sequences in combination with information about a patient's environment and lifestyle, the present invention comes up with a personalized treatment plan, ideally to eliminate the pathogen. It is also possible to use the procedure described above to monitor the course of the disease-state produced by a pathogen. Finally, a genotype-to-phenotype map or database can be constructed for developing better treatments and aiding in research.

Although the above description contains many specificities, these should not be construed as limitations on the scope of the invention but merely as illustrations of some of the presently preferred embodiments. Many other embodiments of the invention are possible. For example, the scripting language and script commands shown are representative of the preferred embodiment. It will be apparent to one skilled in the art many other scripting languages and specific script commands may be used to implement the invention.

Moreover, the invention is not limited to the specific applications described. The system and method of the invention have many other applications both inside and outside the healthcare industry. For example, pharmaceutical manufacturers may apply the system in the clinical development and post marketing surveillance of new drugs, using the system as an interactive, on-line monitoring tool for collecting data on the efficacy, side effects, and quality of life impact of the drugs. Compared to the current use of labor-intensive patient interviews, the system provides a fast, flexible, and cost effective alternative for monitoring the use and effects of the drugs.

The system may also be used by home healthcare companies to enhance the service levels provided to customers, e.g. panic systems, sleep surveillance, specific monitoring of disease conditions, etc. Alternatively, the system may be used to monitor and optimize the inventory of home-stationed health supplies. As an example, the system may be connected to an appropriate measuring device to optimize timing of oxygen tank delivery to patients with chronic obstructive pulmonary disease (COPD).

The system and method of the invention also have many applications outside the healthcare industry. For example, the system may be used for remote education over the Internet, facilitating educational communication with children or adult trainees who lack access to sophisticated and expensive computer equipment. The system may also be used by law enforcement officers to perform on-line surveillance of individuals on probation or parole.

In an alternate embodiment, the software and hardware components of any one of the remote apparatuses 26 or 27 are incorporated directly into a monitoring device. This allows a patient to only have to interact with one device for their entire health monitoring needs.

Further, the invention has numerous applications for gathering data from remotely located devices. For example, the system may be used to collect data from smart appliances, such as identification check systems. Examples of appliances that are used as smart appliances are refrigerator, telephone, stove, clock radio, VCR, or any other electrical or non-electrical device including the monitoring device 28. The smart appliance includes some or all of the components of the remote apparatuses 26 or 27 as illustrated in FIGS. 4 and 15. The smart appliance with the necessary hardware or software components provides all the interactive capabilities described and shown for remote apparatuses 26 or 27, see FIGS. 8–12, 14, 17 and 18. In one embodiment, the assigned scripts are in the form of a recorded voice that is sent over the communication network (e.g. voice over IP) to the appliance or remote apparatus. Also, the user responds to the voice scripts through activation of buttons according to instructions in the voice scripts or by verbally responding to the voice scripts. The verbal responses by the user are sent to the server or workstation over the communication network (e.g. voice over IP). The server or workstation includes a voice recognition component for interpreting the user's verbal responses, records the response and determines the next question or request (verbal or otherwise) to be sent to the user according to the responses. Live voice communication is also possible between the remote apparatus and the server or workstation over the communication network.

Also, the monitoring device includes a communication component for allowing the monitoring device to send data directly to the server 18. The server 18 then sends the monitoring device data to the patient's smart appliance for display to the patient. In an alternate additional setup, the monitoring device sends the data to the smart apparatus.

Alternatively, the system may be applied to the remote monitoring of facilities, including safety and security monitoring, or to environmental monitoring, including pollution control and pipeline monitoring. Many other suitable applications of the invention will be apparent to one skilled in the art.

Therefore, the scope of the invention should be determined not by the examples given, and their legal equivalents.

What is claimed is:

1. A system for remotely monitoring an individual, the system comprising:
   (a) a remote apparatus for interacting with the individual;
   (b) a server system including
      (i) a script generator for generating a script program from a set of health related queries, the script program being executable at the remote apparatus to communicate the set of queries to the individual; and
      (ii) a database for storing the the queries, the responses to the queries, and details of the individual;
   wherein the remote apparatus includes:
      (i) a communication component for receiving the script program from the server and for transmitting the responses to the server;
      (ii) a user interface having an audio transducer for audibly notifying the individual and a display, and
      a processor connected to the user interface for executing the script program to cause presentation on the display of queries to the individual.

2. The system of claim 1, wherein the system is configured to receive script information from a health care provider.

3. The system of claim 2, wherein the system is configured for audibly notifying the individual when unanswered queries are stored at the remote apparatus.

4. The system of claim 1, wherein the system is configured to transmit the script program to the remote apparatus during a first communication link, and a response to at least one query at the central computer through a subsequent communication link.

5. The system of claim 1, wherein the system is configured to transmit at least one script program to the remote apparatus and to receive a response to at least one query wherein the system is configured to transmit at least one script to the remote apparatus and to receive a response to at least one query in the same on-line session in the same on-line session.

6. A method for remotely monitoring an individual comprising:
   generating a script program from a set of queries
   sending the generated script program to a remote apparatus,
   executing the script program at the apparatus to cause communication of at least one of the set of health related queries to the individual;
   receiving responses to at least one of the communicated queries from the individual;
   transmitting the received responses to a central system; and
   storing the transmitted responses and details of the individual at the server system.

7. The method of claim 6, further comprising providing health related service to the individual.

8. The method of claim 6, further comprising audibly notifying the individual when unanswered queries are stored at the remote apparatus.

9. An apparatus for remotely monitoring an individual, apparatus comprising:
   a communication component for receiving a script program from a server wherein the script program represents a set of health related queries;
   a user interface including display and an audio transducer for audibly notifying the individual; and
   a processor for executing the script program to cause communication of at least one of the set of queries to the individual
   wherein the apparatus is configured to
      receive responses to the set of queries from the individual and to transmit the responses to the server; and
      for connection to a monitoring device.

10. The apparatus of claim 9, wherein the monitoring device is one of the set of monitoring devices consisting of a blood glucose meter, a peak flow meter, and an EKG and wherein the apparatus is configured to receive at least one reading from at least one of the monitoring devices and to transmit the reading to the central computer.

11. The apparatus of claim 9, wherein the wherein the apparatus further comprises input buttons configured for use by the individual being queried to enter the responses to queries displayed on the display.

12. The apparatus of claim 9, further comprising a script interpreter that can be programmed during a connection with a central computer.

13. The apparatus of claim 9, wherein the apparatus is configured to receive the script program from a central computer system during a first communication link, and transmit a response to at least one query to the central computer system through a subsequent communication link.

14. The apparatus of claim 9, wherein the apparatus is configured to receive the script program from a central computer system and to transmit a response to at least one query in the same on-line session.

15. A system for remotely querying an individual, the system comprising:
   a. a central computer;
   b. a script generator configured to generate at least one script;
   c. a remote apparatus associated with the individual to be queried;
   d. a communication link
      i. over which communication can be established between the central computer and the remote apparatus and
      ii. over which the generated script can be transmitted to the remote apparatus;
   e. a display associated with the individual to be queried; and
   f. a script interpreter configured
      i. to interpret a script communicated over the communications link and
      ii. to cause display of at least one query related to a health condition of the individual on the display.

16. The system of claim 15 further comprising at least one workstation
   a. in communication with the central computer, and
   b. configured for entering a set of queries to be answered by the individual.

17. The system of claim 15, wherein the display includes at least one response choice for at least one of the queries.

18. The system of claim 17, wherein the script includes at least one program for execution at the remote apparatus.

19. The system of claim 18, wherein the script program further includes display commands to cause display of a plurality of queries and at least one response choice for at least one of the queries.

20. The system of claim 19, wherein the script program further includes a connection command to establish the communication with the central computer at a prescribed connection time and to transmit the at least one response to at least one query to the central computer over the communication link.

21. The system of claim 19, further comprising
   a. a plurality of remote apparatuses each configured for remotely querying a corresponding associated individual,
   wherein the system is configured to
      assign to each of the apparatuses at least one script program and
      to transmit to each of the apparatuses any script program assigned to the apparatus.

22. The system of claim 21, wherein
   a the central computer includes a plurality of sets of queries and corresponding response choices and
   b. the script generator is configured to generate a plurality of script programs from the sets of queries and response choices.

23. The system of claim 22, wherein each of the script programs corresponds to a respective one of the sets of queries and response choices.

24. The system of claim 18, wherein the script interpreter is programmable during a connection with the central computer.

25. The system of claim 18, wherein the system further comprises at least one database for storing
   a. script programs,
   b. a list of the individuals, and
   c. a respective pointer to the script program assigned to each individual.

26. The system of claim 25, wherein the database includes a look-up table.

27. The system of claim 26, wherein the system is configured to
   a. receive an identification code associated with an individual,
   b. use the received identification code to retrieve from the look-up table the pointer to the script assigned to the individual, and
   c. cause the retrieved script to be transmitted to the relevant individual apparatus.

28. The system of claim 17, wherein
   a. the remote apparatus is configured to receive responses to at least one of the queries and
   b. the system is configured to cause the responses to be transmitted to the central computer.

29. The system of claim 17, wherein the system is configured to transmit
   a. the script to the remote apparatus during a first communication link, and
   b. a response to at least one query to the central computer through a subsequent communication link.

30. The system of claim 17, wherein the system is configured to transmit at least one script to the remote apparatus and to receive a response to at least one query in the same on-line session.

31. The system of claim 17, wherein the apparatus includes input buttons configured for use by the individual being queried to enter the responses to queries displayed on the display.

32. The system of claim 17, further comprising a plurality of remote apparatuses each configured for remotely querying a corresponding associated individual.

33. The system of claim 32, wherein the system is configured to assign to each of the individuals at least one script.

34. The system of claim 17, further comprising at least one of the set of monitoring devices consisting of
   a. a blood glucose meter,
   b. a peak flow meter, and
   c. an EKG
and wherein the system is configured to receive at least one reading from at least one of the monitoring devices and to transmit the reading to the central computer.

35. The system of claim 17, further comprising at least one of an audio transducer and an LED for notification to the individual to be monitored.

36. The system of claim 17, wherein the system is configured to use the at least one script to generate a survey.

37. A method for remotely querying an individual, the method comprising:
   generating at least one script;
   establishing a communications link between a central computer and a remote apparatus;
   transmitting the generated script to the remote apparatus via the communication link;

interpreting the script communicated over the communications link; and causing the display of at least one query related to a health condition of the individual on the display, the display being associated with the individual.

38. The method of claim 37, further comprising configuring at least one workstation for entering a set of queries to be answered by the individual, the workstation being operatively in communication with the central computer.

39. The method of claim 37, wherein the display includes at least one response choice for at least one of the queries.

40. The method stem of claim 39, wherein the script includes at least one program for execution at the remote apparatus.

41. The method of claim 40, wherein the script program further includes display commands to cause display of a plurality of queries and at least one response choice for at least one of the queries.

42. The method of claim 41, wherein the script program further includes a connection command to establish the communication with the central computer at a prescribed connection time and to transmit the at least one response to at least one query to the central computer over the communication link.

43. The method of claim 39, further comprising:

receiving responses to at least one of the queries at the remote apparatus; and causing the responses to be transmitted to the central computer.

44. The method of claim 40, which comprises programming the script interpreter during a connection with the central computer.

45. The method of claim 41, further comprising remotely querying a corresponding associated individual via a plurality of remote apparatuses;

assigning to each of the apparatuses at least one script program; and transmitting to each of the apparatuses any script program assigned to the apparatus.

46. The method of claim 45, further comprising:

providing at the central computer a plurality of sets of queries and corresponding response choices; and generating a plurality of script programs from the sets of queries and response choices.

47. The method of claim 46, wherein each of the script programs corresponds to a respective one of the sets of queries and response choices.

48. The method of claim 39, further comprising:

transmitting the script to the remote apparatus during a first communication link; and responding to at least one query to the central computer through a subsequent communication link.

49. The method of claim 39, further comprising:

transmitting at least one script to the remote apparatus; and receiving a response to at least one query in the same on-line session.

50. The method of claim 39, which includes entering responses to queries displayed on the display using input buttons configured for use by the individual being queried.

51. The method of claim 39, further comprising remotely querying a corresponding associated individual associated with one of a plurality of remote apparatuses.

52. The method of claim 51, further comprising assigning to each of the individuals at least one script.

53. The method of claim 39, further comprising storing in at least one database:

a. script programs,
b. a list of the individuals, and
c. a respective pointer to the script program assigned to each individual.

54. The method of claim 53, wherein the database includes a look-up table.

55. The method of claim 54, further comprising:

receiving an identification code associated with an individual, using the received identification code to retrieve from the look-up table the pointer to the script assigned to the individual; and causing the retrieved script to be transmitted to the relevant individual apparatus.

56. The method of claim 39, further comprising monitoring using at least one of the set of monitoring devices consisting of:

a blood glucose meter, a peak flow meter, and an EKG and wherein the method further comprises receiving at least one reading from at least one of the monitoring devices and transmitting the reading to the central computer.

57. The method of claim 39, further comprising notifying the individual to be monitored using at least one of an audio transducer and an LED.

58. The method of claim 39, further comprising using the at least one script to generate a survey.

59. Remote apparatus for use in the method of claim 37.

60. A central computer for use in the method of claim 37.

61. A computer program product for executing a set of instructions that, when executed by computer device, cause the computer device to:

generate at least one script;

establish a communications link between a central computer and a remote apparatus;

transmit the generated script to the remote apparatus via the communication link;

interpret the script communicated over the communications link; and cause the display of at least one query related to a health condition of an individual on the display, the display being associated with the individual.

62. The computer program product of claim 61, which configures at least one workstation for entering a set of queries to be answered by the individual, the workstation being operatively in communication with the central computer.

63. The computer program product of claim 61, which configures the display to include at least one response choice for at least one of the queries.

64. The computer program product stem of claim 63, wherein the script includes at least one program for execution at the remote apparatus.

65. The computer program product of claim 64, wherein the script program further includes display commands to cause display of at least one of a plurality of queries and at least one response choice for at least one of the queries.

66. The computer program product of claim 65, wherein the script program further includes a connection command to establish the communications link with the central computer at a prescribed connection time and to transmit the at least one response to at least one query to the central computer over the communication link.

67. A system for remotely querying an individual, the system comprising:
- means for generating at least one script;
- means for establishing a communications link between a central computer and a remote apparatus;
- means for transmitting the generated script to the remote apparatus via the communication link;
- means for interpreting the script communicated over the communications link; and
- means for causing the display of at least one query related to a health condition of the individual on the display, the display being associated with the individual.

* * * * *

UNITED STATES PATENT AND TRADEMARK OFFICE
CERTIFICATE OF CORRECTION

| | | |
|---|---|---|
| PATENT NO. | : 6,968,375 B1 | Page 1 of 1 |
| APPLICATION NO. | : 09/658209 | |
| DATED | : November 22, 2005 | |
| INVENTOR(S) | : Stephen J. Brown | |

It is certified that error appears in the above-identified patent and that said Letters Patent is hereby corrected as shown below:

Column 5, line 46, delete "Appendix A" and insert -- Figure 6 --.

Column 21, line 57, delete "the" (second occurrence).

Signed and Sealed this

Seventeenth Day of April, 2007

JON W. DUDAS
*Director of the United States Patent and Trademark Office*